(12) United States Patent
Cheng

(10) Patent No.: US 11,437,225 B2
(45) Date of Patent: Sep. 6, 2022

(54) METHOD AND SYSTEM FOR DETERMINING ENERGY SPECTRUM OF X-RAY DEVICE

(71) Applicant: SHANGHAI UNITED IMAGING HEALTHCARE CO., LTD., Shanghai (CN)

(72) Inventor: Peng Cheng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/452,860

(22) Filed: Jun. 26, 2019

(65) Prior Publication Data

US 2020/0176237 A1 Jun. 4, 2020

(30) Foreign Application Priority Data

Nov. 30, 2018 (CN) .......................... 201811458575.2

(51) Int. Cl.
| | |
|---|---|
| *H01J 49/00* | (2006.01) |
| *A61N 5/10* | (2006.01) |
| *H01J 49/20* | (2006.01) |
| *H01J 49/44* | (2006.01) |

(52) U.S. Cl.
CPC ........ *H01J 49/0027* (2013.01); *A61N 5/1065* (2013.01); *H01J 49/20* (2013.01); *A61N 2005/1089* (2013.01); *H01J 49/44* (2013.01)

(58) Field of Classification Search
None
See application file for complete search history.

(56) References Cited

U.S. PATENT DOCUMENTS

| | | | | |
|---|---|---|---|---|
| 5,895,916 A | * | 4/1999 | Tsukajima | H01J 37/256 250/305 |
| 6,066,852 A | * | 5/2000 | Taya | H01J 37/05 250/305 |
| 8,710,452 B2 | * | 4/2014 | Henstra | H01J 37/26 250/396 R |
| 8,952,340 B2 | * | 2/2015 | Kabasawa | H01J 37/05 250/306 |

(Continued)

FOREIGN PATENT DOCUMENTS

| | | | |
|---|---|---|---|
| CN | 102207462 A | * | 10/2011 |
| CN | 202161697 U | | 3/2012 |

(Continued)

*Primary Examiner* — Andrew Smyth
(74) *Attorney, Agent, or Firm* — Metis IP LLC

(57) ABSTRACT

The present disclosure discloses a method and a system for determining an energy spectrum of an incident electron beam. The method includes obtaining a plurality of deflection currents of a beam deflection device; for each of the plurality of deflection currents, determining an energy range of an ejected electron beam, and determining a target current of a target generated by the ejected electron beam irradiating the target, wherein the ejected electron beam is emitted from an output of the beam deflection device after the incident electron beam enters the beam deflection device. The method also includes determining the energy spectrum of the incident electron beam based on the energy ranges of the plurality of ejected electron beams and the corresponding target currents.

20 Claims, 12 Drawing Sheets

(56) References Cited

U.S. PATENT DOCUMENTS

| | | | | |
|---|---|---|---|---|
| 2012/0241604 A1* | 9/2012 | Watanabe | ............... | G01L 21/32 |
| | | | | 250/288 |
| 2013/0231516 A1 | 9/2013 | Loo et al. | | |
| 2016/0086762 A1* | 3/2016 | de Jong | ............... | H01J 37/285 |
| | | | | 250/305 |
| 2018/0277276 A1* | 9/2018 | Purwar | .................... | G21K 5/04 |

FOREIGN PATENT DOCUMENTS

| | | | | |
|---|---|---|---|---|
| CN | 102207462 B | * | 5/2013 | |
| CN | 107789749 A | | 3/2018 | |
| CN | 107942370 A | | 4/2018 | |
| JP | H0194867 A | | 4/1989 | |
| JP | 04282547 A | * | 10/1992 | |
| JP | 07021966 A | * | 1/1995 | |

* cited by examiner

METHOD AND SYSTEM FOR DETERMINING ENERGY SPECTRUM OF X-RAY DEVICE

CROSS REFERENCE TO RELATED APPLICATIONS

This application claims priority to Chinese Application No. 201811458575.2 filed on Nov. 30, 2018, the entire contents of which are hereby incorporated by reference.

TECHNICAL FIELD

The present disclosure relates to an X-ray device, and more particularly to a method and system for determining the energy spectrum of an electron beam generated in an X-ray device.

BACKGROUND

Radiation therapy has become widespread. Clinically, for a specific treatment, a desired radiation dose needs to be delivered to a treatment area, and an actually delivered radiation dose needs to be sufficiently accurate. For example, the deviation of an actually delivered radiation dose from a desired radiation dose needs to be less than 5%. Therefore, information of the actual energy spectrum of an electron beam is of great significance for radiation dose delivery and/or monitoring.

SUMMARY

Embodiments of the present disclosure provide a method, a system, an apparatus, and a computer readable storage medium for determining an energy spectrum of an electron beam. Specifically, it may include the following aspects.

In a first aspect, the present disclosure discloses a process for determining an energy spectrum of an incident electron beam. The process may include obtaining a plurality of deflection currents of a beam deflection device. The process may also include for each of the plurality of deflection currents, determining an energy range of an ejected electron beam and determining a target current of a target generated by the ejected electron beam irradiating the target, wherein the ejected electron beam is emitted from an output of the beam deflection device after an incident electron beam enters the beam deflection device. The process may further include determining the energy spectrum of the incident electron beam based on the energy ranges of the plurality of ejected electron beams and the corresponding target currents.

In some embodiments, the process may further include determining a magnetic field strength generated by the beam deflection device based on the deflection current and determining a center energy value of the energy range of the ejected electron beam based on the magnetic field strength and a deflection radius of the beam deflection device. The process may also include determining the energy range of the ejected electron beam based on the center energy value and a width of the energy range.

In some embodiments, the process may further include determining a plurality of energy sub-ranges of the incident electron beam by dividing the incident electron beam based on the energy ranges of the plurality of ejected electron beams and determining a plurality of sub-currents based on the target currents corresponding to the energy ranges of the plurality of ejected electron beams, each sub-current corresponding to an energy sub-range of the plurality of the energy sub-ranges. The method may also include determining the energy spectrum of the incident electron beam based on the plurality of sub-currents corresponding to the plurality of energy sub-ranges of the incident electron beam.

In some embodiments, the process may include obtaining a target deflection current of the beam deflection device and determining an energy range of a target ejected electron beam. The target ejected electron beam may be emitted from the output of the beam deflection device after the incident electron beam enters the beam deflection device. The process may further include determining an energy spectrum of the target ejected electron beam based on the energy range of the target ejected electron beam and the energy spectrum of the incident electron beam.

In some embodiments, the beam deflection device may include an energy slit. The energy slit may be configured to allow electrons in the incident electron beam whose energies fall within a range to pass through.

In some embodiments, the process may further include gradually changing the deflection current of the beam deflection device, and successively obtaining the target current flowing through the target when each of the plurality of ejected electron beams irradiates the target.

In some embodiments, the energy ranges of the plurality of ejected electron beams may be continuously distributed.

In some embodiments, a start-point of the energy range of an ejected electron beam may coincide with an end-point of the energy range of at least one ejected electron beam generated prior to the ejected electron beam, or an end-point of the energy range of the ejected electron beam may coincide with a start-point of the energy range of at least one ejected electron beam generated prior to the ejected electron beam.

In some embodiments, the target current of the target generated by at least one specific ejected electron beam of the plurality of the ejected electron beams irradiating the target may be 0. Each of the plurality of ejected electron beams other than the at least one specific ejected electron beam may meet at least one of the following conditions: (1) the energy range of the each ejected electron beam at least partially overlaps with the energy range of the at least one specific ejected electron beam; or (2) a start-point or an end-point of the energy range of the each ejected electron beam coincides with a start-point or an end-point of the energy range of any ejected electron beam generated prior to the each ejected electron beam.

In a second aspect, the present disclosure discloses a system for determining an energy spectrum of an incident electron beam. The system may include a beam deflection device and a computing device. The computing device may include a processor, wherein during operations, the processor may cause the system to obtain a plurality of deflection currents of the beam deflection device. The processor may cause the system further to, for each of the plurality of deflection currents, determine an energy range of an ejected electron beam, wherein the ejected electron beam is emitted from an output of the beam deflection device after the incident electron beam enters the beam deflection device, and determine a target current of a target generated by the ejected electron beam irradiating the target. The processor may cause the system further to determine the energy spectrum of the incident electron beam based on the energy ranges of the plurality of ejected electron beams and the corresponding target currents.

In a third aspect, the present disclosure discloses a non-transitory computer readable medium including executable instructions that, when executed by at least one processor, may cause the at least one processor to effectuate a process. The process may include obtaining a plurality of deflection currents of a beam deflection device. The process may also include for each of the plurality of deflection currents, determining an energy range of an ejected electron beam and determining a target current of a target generated by the ejected electron beam irradiating the target, wherein the ejected electron beam is emitted from an output of the beam deflection device after an incident electron beam enters the beam deflection device. The process may further include determining the energy spectrum of the incident electron beam based on the energy ranges of the plurality of ejected electron beams and the corresponding target currents.

Some of the additional features of the present disclosure can be explained in the following description. Some of the additional features of the present disclosure will be apparent to those skilled in the art from a review of the following description and the accompanying drawings. The features of the present disclosure may be realized and attained by practice or use of various aspects of the methodologies, instrumentalities, and combinations set forth in the detailed examples discussed below. Because of the above technical solutions, methods and systems described in the present disclosure have at least the following technical effects: there is no need to insert an energy spectrum measurement and/or monitoring device into the accelerating tube system for measuring and/or monitoring the energy spectrum of an electron beam. Instead, a plurality of energy ranges of an electron beam emitted from the beam deflection device and the corresponding target currents may be obtained by adjusting the deflection current of the beam deflection device. Thereby, the energy spectrum information of the electron beam emitted from the accelerating tube may be determined. In some embodiments, based on a deflection current, and based on the determined energy spectrum of an electron beam emitted from the accelerating tube, the energy spectrum distribution of an electron beam emitted from the output end of the beam deflection device may be obtained.

BRIEF DESCRIPTION OF THE DRAWINGS

The present disclosure is further described in terms of exemplary embodiments. The exemplary embodiments are described in detail with reference to the accompanying drawings. The drawings are not to scale. The embodiments are non-limiting embodiments, in which the same reference numerals represent similar structures throughout the several views of the drawings, and wherein.

DETAILED DESCRIPTION

Figure 1:
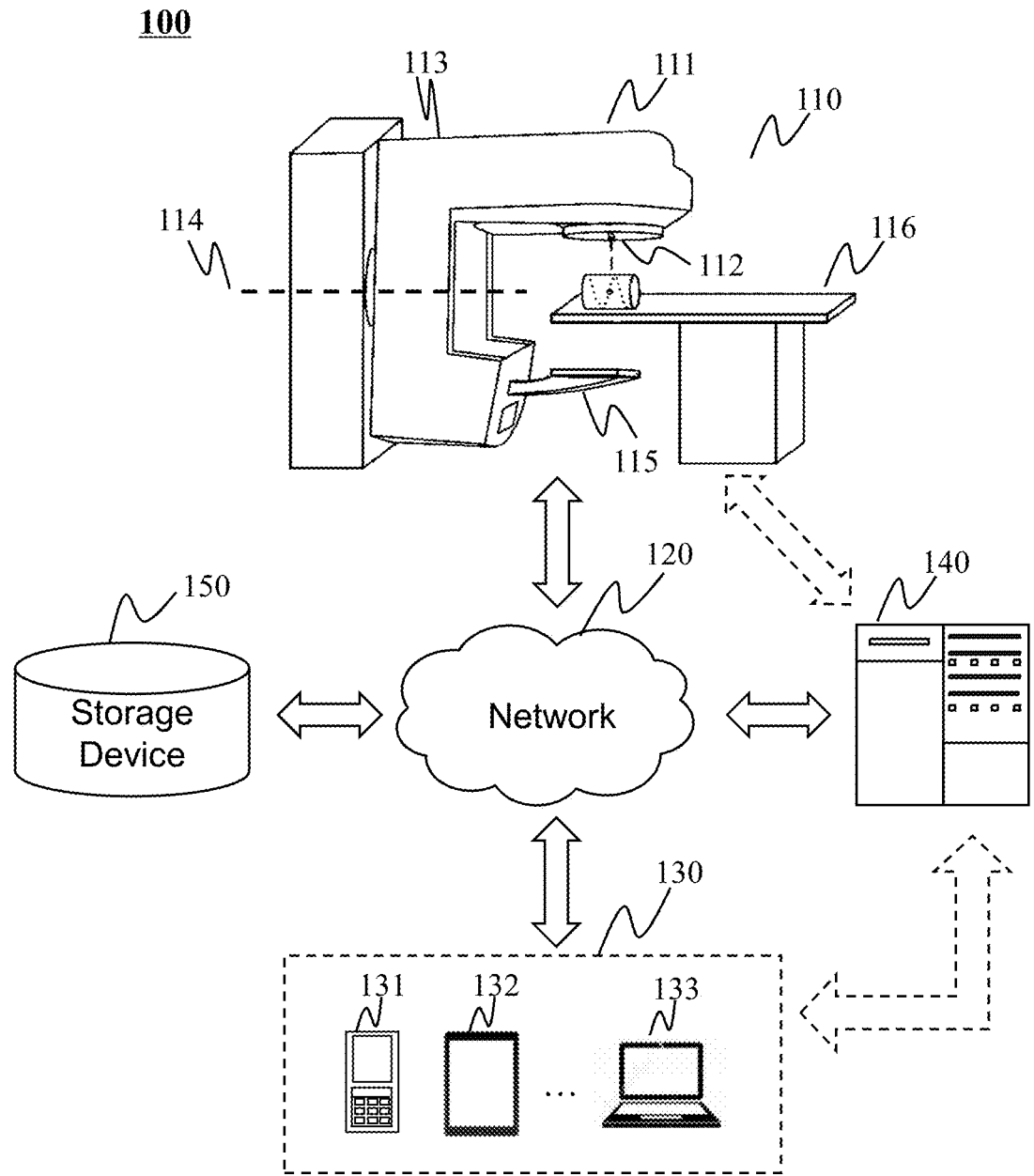
FIG. 1 is a schematic diagram of an exemplary radiation therapy system according to some embodiments of the present disclosure.

In the following detailed description, the specific details of the present disclosure are set forth by the embodiments in order to provide a thorough understanding of the related application. Various modifications to the embodiments of the present disclosure will be apparent to those skilled in the art, and the general principles defined by the present disclosure may be applied to other embodiments and applications scenarios without departing from the spirit and the scope of the present disclosure. Therefore, the present disclosure is not limited to the embodiments shown, but to be accorded the broadest scope consistent with the claims.

The terminology used in the present disclosure is only for the purpose of describing a particular exemplary embodiment, and it is non-limiting. As used by the present disclosure, unless the context clearly indicates an exception, the singular forms "a," "an," and "the" may also include the plural. It should be further understood that the terms "including" and "comprising," when used in the present specification, mean the presence of the features, integer constants, steps, operations, elements and/or components. However, it is not excluded to exist or add one or more other features, integer constants, steps, operations, elements, components, and/or combinations thereof.

It should be understood that the terms "system," "engine," "unit," "module," and/or "block" used by the present disclosure are one method to distinguish different components, elements, parts, section or components in ascending order. However, if other expressions achieve the same purpose, these terms may be replaced by other expressions.

Generally, a "module," "unit," or "block," as used in the present disclosure, refers to logic embodied in a collection of hardware, firmware or software instructions. The modules, unit or blocks described by the present disclosure may be executed on the software and/or the hardware and may be stored in any type of non-transitory computer readable medium or another storage device. In some embodiments, the software, the module, the unit, and the blocks may be compiled and connected to the executable strip. It should be understood that the software module may be called from other modules, units, blocks or themselves and/or may be invoked in response to detected events or interruptions. The software module/unit/block (e.g., the processor 210 in FIG. 2) configured for execution on a computing device may be provided on the computer readable medium, such as an optical disc, a digital video disc, a flash drive, a disk, any other tangible medium or as a digital download (and may be originally stored in a compressed or a installable format, which needs to be installed, decompressed or decrypted prior to execution). The software code may be stored, in part or in whole, on a storage device executing the computing device for execution by the computing device. Software instructions may be embedded in the firmware, such as an EPROM. It should be understood that the hardware modules, the unit or the blocks may be included in the connected logic components, such as gates and flip-flops and/or may be included in a programmable unit such as a programmable gate array or a processor. The module, the unit, the block or the computing device function described by the present disclosure may be implemented as the software module/unit/block, but may be represented by the hardware or the firmware. Generally, the module, the unit, and the blocks described herein refer to logical modules, units, and blocks that may be combined with other modules, units, and blocks, or divided into sub-modules, sub-units, and sub-blocks, despite their physical organization or storage. The description may apply to the system, the engine, or a portion thereof.

It should be understood that when the unit, the engine, the module or the block is referred to as "on," "connected," or "coupled" to another unit, engine, module or block. It may communicate directly in another unit, engine, module, or block, or can have a unit, an engine, a module, or a block, unless the context clearly indicates an exception. As used in the present disclosure, the term "and/or" includes any and all combinations of one or more of the listed items.

Provided herein is a system having a plurality of movable components for medical or industrial applications. For example, for disease treatment, disease diagnosis, synchronized motion control, research purposes, or the like. In some embodiments, the system may be a combination of one or more of a radiation therapy (RT) system, a computed tomography (CT) system, an ultrasound inspection system, an X-ray imaging system, or the like. The following description is provided with reference to the RT system for illustrative purposes and is not intended to limit the scope of the present disclosure.

FIG. 1 is a schematic diagram of an exemplary radiation therapy system according to some embodiments of the present disclosure.

As shown in FIG. 1, the radiation therapy system 100 may include a radiation therapy device 110, a network 120, one or more terminals 130, a processing device 140, and a storage device 150.

The radiation therapy device 110 may deliver a radiation beam to a target subject (e.g., a patient or a phantom). In some embodiments, the radiation therapy device 110 may include a linear accelerator 111. The linear accelerator 111 may generate and emit a radiation beam (e.g., X-rays) from a treatment head 112. The radiation beam may pass through one or more collimators having a particular shape (e.g., a multi-leaf grating) and get to the target object. In some embodiments, the radiation beam may include X-rays, electrons, photons or any other type of radiation. The treatment head 112 may be coupled to a gantry 113. The gantry 113 may be rotated, for example, clockwise or counterclockwise around a frame axis 114. The treatment head 112 may rotate with the gantry 113. In some embodiments, the radiation therapy device 110 may include an imaging component 115. The imaging component 115 may receive radiation beams passing through the target subject and may acquire an image of the patient or the phantom. The image may be acquired by the imaging component 115 before, during, and/or after the radiation therapy or correction procedure. The imaging component 115 may include an analog detector, a digital detector, or any combination thereof. The imaging component 115 may be connected to the gantry 113 in any manner, including an expandable and telescoping housing. Thus, the treatment head 112 and the imaging component 115 may be rotated with the gantry 113 synchronously. In some embodiments, the radiation therapy device 110 may also include a couch 116. The couch 116 may support the patient during the radiation therapy or the imaging, and/or support the phantom during a calibration of the radiation therapy device 110. The couch 116 may be adjusted for different scenarios.

A network 120 may include any suitable network capable of facilitating the information and/or data exchange of the radiation therapy system 100. In some embodiments, the one or more components of the radiation therapy system 100 (e.g., the radiation therapy device 110, the one or more terminals 130, the processing device 140, the storage device 150, etc.) may exchange information and/or data between the network 120 and one or more components of the radiation therapy system 100. For example, the processing device 140 may obtain planning data from a radiation treatment planning system (TPS) over the network 120.

The one or more terminals 130 may include a mobile device 131, a tablet computer 132, a laptop computer 133, or the like, or any combination thereof. The one or more terminals 130 may be used to control the radiation therapy device 110. A user may control the parameters of a plurality of components of the radiation therapy device 110 through the one or more terminals 130. For example, the user may control the height of the couch 116 of the radiation therapy device 110 via the one or more terminals 130. The user may control the radiation therapy device 110 via the one or more terminals 130 to perform the radiation therapy on the patient. The user may control a radiation dose of the radiation therapy device 110 to the patient via the one or more terminals 130. The user may set a deflection current of the beam deflection device (or beam deflection device) in the radiation therapy device 110 through the one or more terminals 130. By changing the deflection current, the intensity of the magnetic field produced by the beam deflection device may vary.

In some embodiments, the one or more terminals 130 may be part of the processing device 140. The processing device 140 may process data and/or information obtained from the radiation therapy device 110, the one or more terminals 130, and/or the storage device 150. For example, the processing device 140 may process the planning data and determine motion parameters for controlling motions of the plurality of components of the radiation therapy device 110. As another example, the processing device 140 may obtain a plurality of deflection currents of the beam deflection device. The processing device 140 may determine an energy range of each of a plurality of ejected electron beams emitted from the output of the beam deflection device after the incident electron beam enters the beam deflection device based on each deflection current. The processing device 140 may obtain a target current flowing through a target after each of the plurality of ejected electron beams irradiates the target. The target may be used to generate radiation after irradiated by each of the plurality of ejected electron beams. The processing device 140 may determine an energy spectrum of the incident electron beam based on the energy ranges of the plurality of ejected electron beams and a plurality of the target currents corresponding to the plurality of ejected electron beams. In some embodiments, the processing device 140 may be a single server or a server group. The server group may be centralized or distributed. In some embodiments, the processing device 140 may be local or remote. For example, the processing device 140 may access information and/or data from the radiation therapy device 110, the one or more terminals 130, and/or the storage device 150 over the network 120. As another example, the processing device 140 may directly connect the radiation therapy device 110, the one or more terminals 130, and/or the storage device 150 to access information and/or data.

The storage device 150 may store data, instructions, and/or any other information. In some embodiments, the storage device 150 may store data obtained from the processing device 140 and/or the one or more terminals 130. In some embodiments, the storage device 150 may store data and/or instructions that the processing device 140 may perform or use to perform the example methods described in the present disclosure. In some embodiments, the storage device 150 may include one or a combination of a mass memory, a removable memory, a volatile read/write memory, a read only memory (ROM), or the like. The mass memory may include disks, compact discs, solid state drives, removable storage, or the like. The removable memory may include a flash drive, a floppy disk, an optical disk, a memory card, a ZIP disk, a magnetic tape, or the like. The volatile read/write memories may include a random access memory (RAM). The RAM may include a dynamic random access memory (DRAM), a double data rate synchronous dynamic a random access memory (DDR-SDRAM), a static random access memory (SRAM), a thyristor random access memory (T-RAM), a zero capacitance random access memory (Z-RAM), or the like. The ROM may include a mask read only memory (MROM), a programmable read only memory (PROM), an erasable programmable read only memory (EPROM), an electrically erasable programmable read only memory (EEPROM), a compact disk read only memory (CD-ROM), an optical disc of digital multifunction optical disc, or the like. In some embodiments, the storage device 150 may be implemented by a cloud platform described in the present disclosure. For example, the cloud platform may include one or a combination of a private cloud, a public cloud, a hybrid cloud, a community cloud, a distributed cloud, a cross cloud, an inter-cloud, a multi-cloud, or the like.

In some embodiments, the storage device 150 may be connected to the network 120 to effectuate communication with one or more components (e.g., the processing device 140, the one or more terminals 130, etc.) in the radiation therapy system 100. The one or more components of the radiation therapy system 100 may retrieve data or instructions from the storage device 150 via the network 120. In some embodiments, the storage device 150 may be part of the processing device 140.

Figure 2:
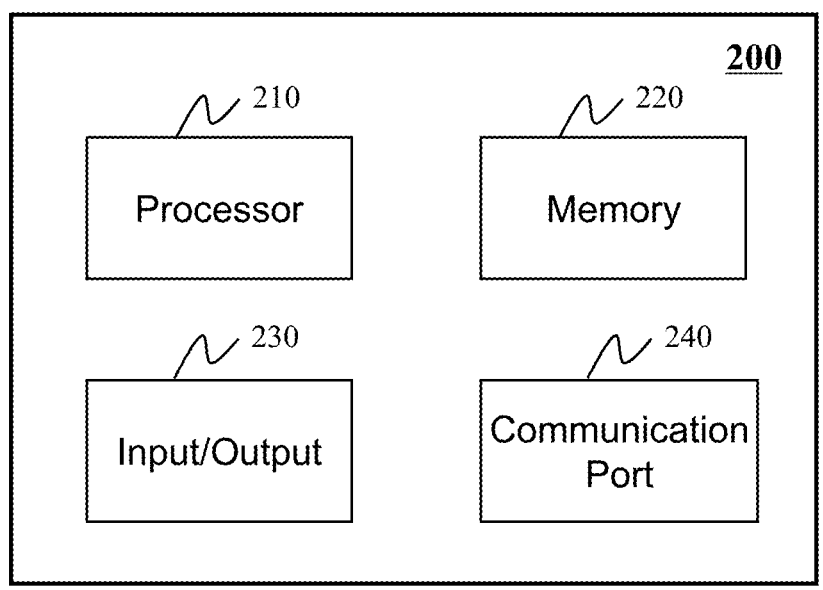
FIG. 2 is a schematic diagram of hardware and/or software components of an exemplary computing device according to some embodiments of the present disclosure.

FIG. 2 is a schematic diagram of hardware and/or software components of an exemplary computing device according to some embodiments of the present disclosure.

As shown in FIG. 2, the computing device 200 may include a processor 210, a memory 220, an input/output (I/O) 230, and a communication port 240.

The processor 210 may execute computer instructions (e.g., program code) and may execute the functions of the processing device 140 in accordance with the techniques described in the application. The computer instructions may be used to execute the particular functions described in the present disclosure, which may include, for example, programs, objects, components, data structures, programs, modules, and functions. For example, the processor 210 may process the planning data obtained from the storage device 150, and/or any other component of the radiation therapy system 100. In some embodiments, the processor 210 may include one or more hardware processors such as a combination of one or more of a microcontroller, a microprocessor, a reduced instruction set computer (RISC), an application specific integrated circuit (ASIC), an application-specific instruction-set processor (ASIP), a central processing unit (CPU), a graphics processing unit (GPU), a physics processing unit (PPU), a digital signal processor (DSP), a field programmable gate array (FPGA), an advanced RISC machine (ARM), a programmable logic device (PLD), any circuit capable of performing one or more functions, or a processor.

For illustration purpose, only one processor is depicted in the computing device 200. However, it should be noted that the computing device 200 may also include a plurality of processors. The operations and/or methods performed by the processor described in the present disclosure may also be performed jointly or separately by a plurality of processors. For example, if the processor of the computing device 200 described in the present disclosure performs operation A and operation B, it should be understood that operation A and operation B may also be performed jointly or separately by two or more different processors in the computing device 200 (for example, the first processor performs operation A and the second processor performs operation B, or the first processor and the second processor perform operations A and B together).

The memory 220 may store data/information obtained from the radiation therapy device 110, the one or more terminals 130, the storage device 150, and/or any other component of the radiation therapy system 100. In some embodiments, the memory 220 may include at least one of a mass memory, a removable memory, a volatile read/write memory, a read only memory (ROM), or the like, or any combination thereof. The mass memory may include disks, compact discs, solid state drives, removable storage, or the like. The removable memory may include a flash drive, a floppy disk, an optical disk, a memory card, a ZIP disk, a magnetic tape, or the like. The volatile read/write memories may include a random access memory (RAM). The RAM may include a dynamic random access memory (DRAM), a double data rate synchronous dynamic random access memory (DDR SDRAM), a static random access memory (SRAM), a thyristor random access memory (t-ram), a zero capacitor random access memory (Z-RAM), or the like. The ROM may include a mask read only memory (MROM), a programmable read only memory (PROM), a erasable programmable read only memory (EPROM), an electrically erasable programmable read only memory (EEPROM), a compact disk read only memory (CD-ROM), an optical disk of a digital multifunction optical disk, or the like. In some embodiments, the memory 220 may store one or more programs and/or instructions for performing the example methods described in the present disclosure. For example, the memory 220 may store programs that may be used by the processing device 140 to determine motion parameters for multiple components.

The input/output 230 may input and/or output signals, data, information, or the like. In some embodiments, the input/output 230 may facilitate interaction between a user and the processing device 140. In some embodiments, the input/output 230 may include an input device and an output device. The input device may include at least one of a keyboard, a mouse, a touch screen, a microphone, or the like, or any combination thereof. The output device may include at least one of a display device, a speaker, a printer, a projector, or the like, or any combination thereof. The display device may include at least one of a liquid crystal display (LCD), a light emitting diode (LED) display, a flat panel display, a curved screen, a television device, a cathode ray tube (CRT), a touch screen, or the like, or any combination thereof.

The communication port 240 may be connected to a network (e.g., network 120) to facilitate data communication. The communication port 240 may establish a connection between the processing device 140 and the radiation therapy device 110, the one or more terminals 130, and/or the storage device 150. The connection may be at least one of a wired connection, a wireless connection, any connection capable of data transmission and/or reception, or the like, or any combination thereof. The wired connection may include, for example, at least one of a cable, a fiber optic cable, a telephone line, or the like, or any combination thereof. The wireless connection may include, for example, at least one of a Bluetooth™ link, a Wi-Fi™ link, a WiMAX™ link, a wireless local area network link, a ZigBee™ link, a mobile network link (e.g., 3G, 4G, 5G, etc.). In some embodiments, the communication port 240 may include a standardized communication port, such as RS232, RS485, etc. In some embodiments, the communication port 240 may be a specially designed communication port. For example, the communication port 240 may be designed in accordance with a digital imaging and a communication in the medical (DICOM) protocol.

Figure 3:
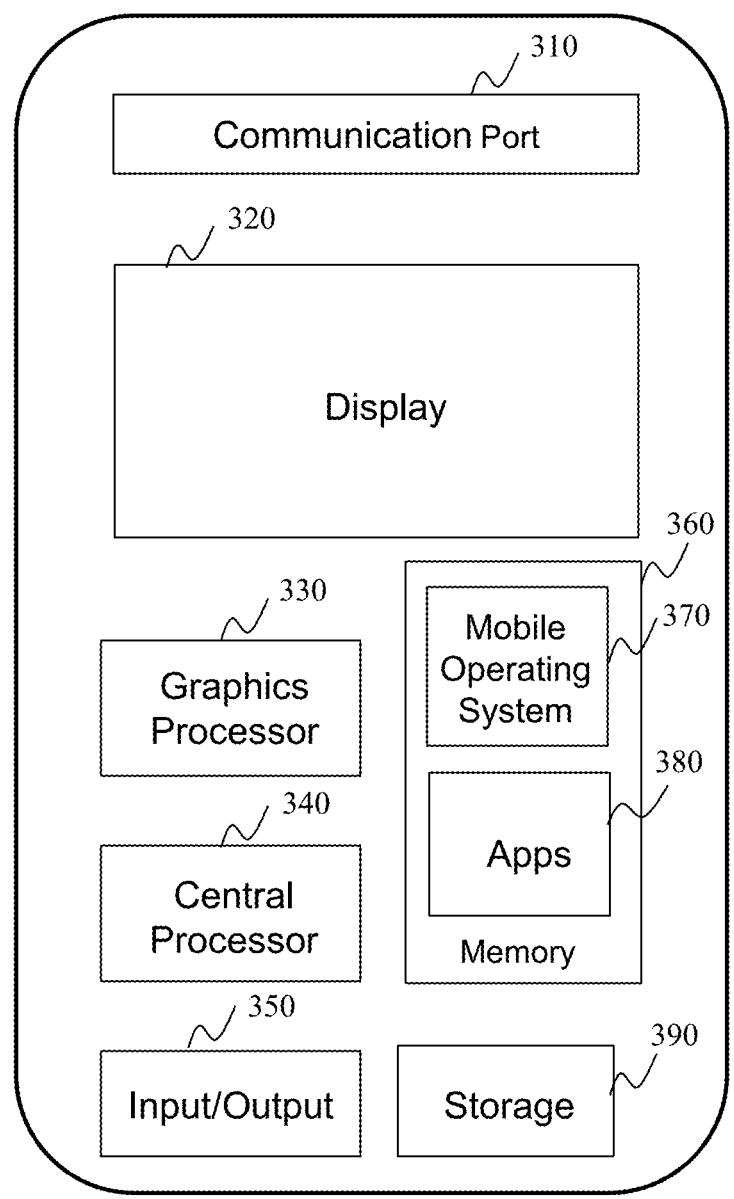
FIG. 3 is a schematic diagram of hardware and/or software components of an exemplary mobile device according to some embodiments of the present disclosure.

FIG. 3 is a schematic diagram of hardware and/or software components of an exemplary mobile device 300 that may implement the one or more terminals 130 according to some embodiments of the present disclosure.

As shown in FIG. 3, the mobile device 300 may include a communication port 310, a display 320, a graphics processor (GPU) 330, a central processor (CPU) 340, an input/output 350, a memory 360, and a storage 390. In some embodiments, the mobile device 300 may also include any other suitable components including, but not limited to, a system bus or a controller (not shown). In some embodiments, a mobile operating system 370 (e.g., iOS™, Android, Windows Phone™, etc.) and one or more applications 380 may be loaded into the memory 360 from the storage 390 so as to be executable by the central processor 340. The applications 380 may include a browser or any other suitable mobile applications for receiving and presenting information related to the image processing or other information from the processing device 140. User interaction of the information flow may be implemented by the input/output 350 and provided to the processing device 140 and/or other components of the radiation therapy system 100 via the network 120.

To implement the various modules, units, and functions described in the present disclosure, a computer hardware platform may be used as the hardware platform for one or more elements described in the present disclosure. A computer with user interface elements may be used to implement a personal computer (PC) or any other type of workstation or terminal device. The computer may also act as a server if properly programmed.

Figure 4:
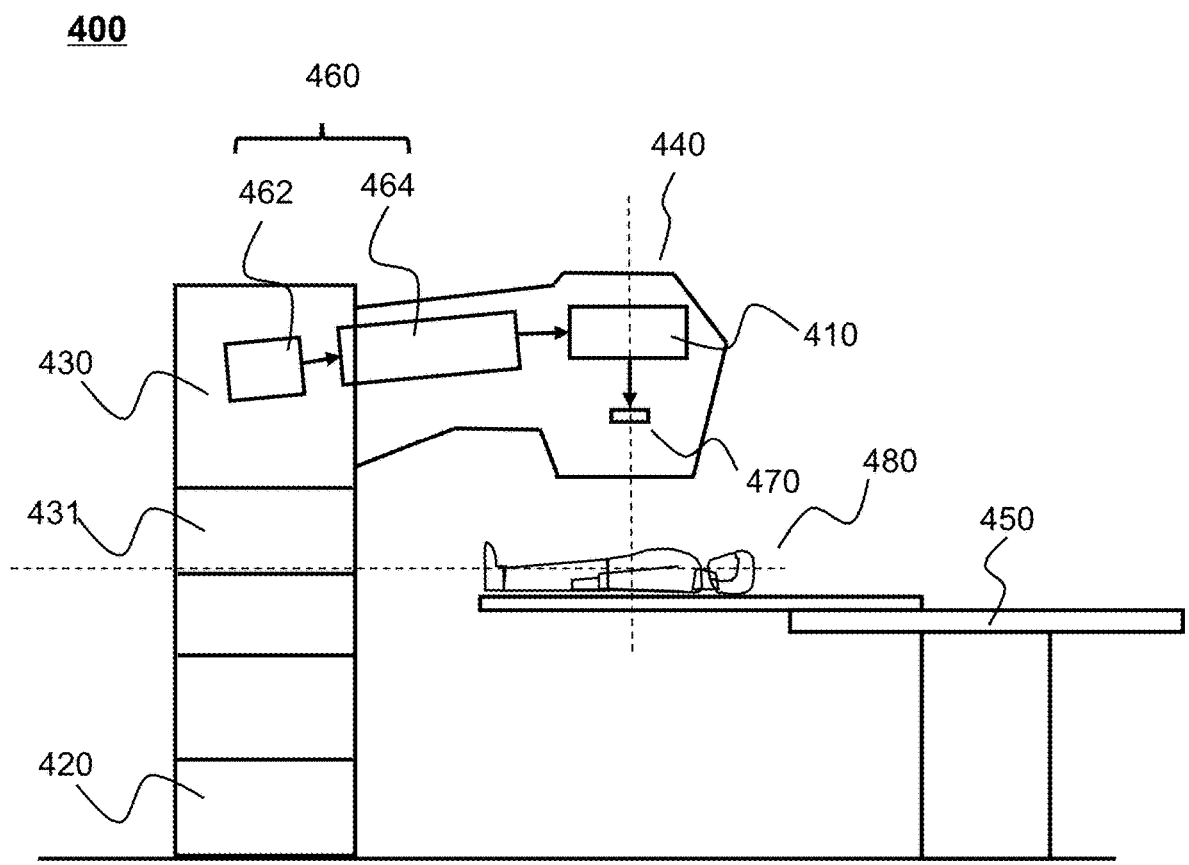
FIG. 4 is a schematic diagram of an exemplary radiation therapy device according to some embodiments of the present disclosure.

FIG. 4 is a schematic diagram of an exemplary radiation therapy device according to some embodiments of the present disclosure.

As shown in FIG. 4, the radiation therapy device 400 may include a base 420, a rotating gantry 430, a treatment head 440, and a couch 450.

A through-hole 431 may be disposed in the rotating gantry 430. The rotating gantry 430 may be rotatably disposed on the base 420 so that the rotating gantry 430 may rotate around a rotating axis. The treatment head 440 may be connected to the rotating gantry 430 and rotate along with the rotating gantry 430. The rotating gantry 430 may rotate to adjust the angle of the treatment head 440 relative to a patient 480 lying on the couch 450 to adjust the radiation distribution irradiated in the patient 480. A charged particle beam emitting device 460 may be disposed within the rotating gantry 430.

The treatment head 440 may be used to irradiate an imaging radiation or a treatment radiation (e.g., X-rays) on the patient 480. A beam deflection device 410 and a target 470 may be provided in the treatment head 440.

The charged particle beam emitting device 460 may be used to generate an electron beam and accelerate the electron beam. The charged particle beam emitting device 460 may include an electron gun 462 and an accelerating tube 464. The accelerating tube 464 may be connected with the electron gun 462 and located between the electron gun 462 and the beam deflection device 410. The electron gun 462 may be used to generate electron beams. An electron beam may be accelerated in the accelerating tube 464 to a desired speed to meet the energy level requirements for imaging or therapy. The beam deflection device 410 may be used to deflect an accelerated electron beam and direct it to the couch 450. The target 470 may be irradiated by the electron beam emitted from the beam deflection device 410 to generate radiations. The electron beam may irradiate the target 470 to produce a therapeutic or an imaging radiation. In some embodiments, the target 470 may be a moving target in order to switch between different modes including, e.g., an imaging mode, a treatment mode, or other modes.

The beam deflection device 410 may be located downstream of the charged particle beam emitting device 460 in the propagation direction of the electron beam emitted by the electron gun 462. The propagation path of the electron beam after deflection may be substantially directed to the couch 450. The target 470 may be located downstream of the beam deflection device 410 to be irradiated by the electron beam emitted from the beam deflection device 410 so as to produce radiations such as therapeutic radiations, imaging radiations, or the like. The arrangement of the base 420, the rotating gantry 430, the treatment head 440 and the couch 450 of the radiation therapy device 400 may be various, which is not limited to the exemplary embodiments shown herein. The type of the accelerating tube 464 may be a traveling wave accelerating tube or a standing wave accelerating tube.

Figure 5:
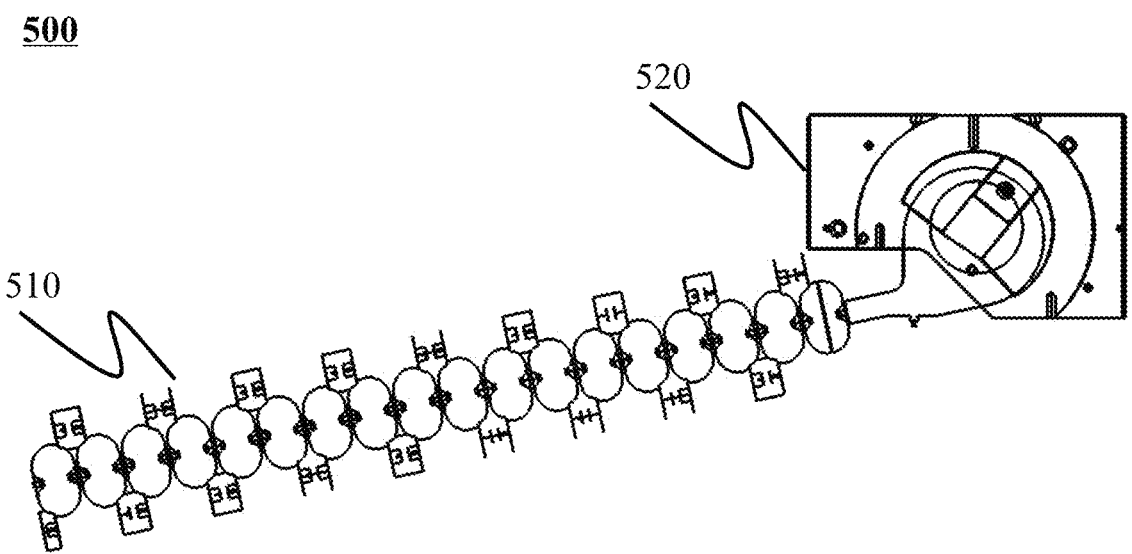
FIG. 5 is a schematic diagram of an exemplary standing wave accelerating tube according to some embodiments of the present disclosure.

FIG. 5 is a schematic diagram of an exemplary accelerating tube according to some embodiments of the present disclosure.

The accelerating tube 500 may include a standing wave accelerating tube 510 and a beam deflection device 520. The standing wave accelerating tube 510 may include a medium energy standing wave accelerating tube. The standing wave accelerating tube 510 may accelerate the incident electron beam. The incident electron beam emitted from the standing wave accelerating tube 510 may enter the beam deflection device 520. The beam deflection device 520 may deflect the incident electron beam. An energy slit in the beam deflection device 520 may permit electrons in the incident electron beam whose energies fall within a certain range to pass through and emitted from the output of the beam deflection device 520 (for example, the output window of the vacuum box in the beam deflection device 520). An ejected electron beam formed by the electrons passing through the energy slit and emitted from the output of the beam deflection device 520 may irradiate the target, and the target may radiate radiations (for example, X-rays). The ejected electron beam may be a part of the incident electron beam with a specific energy range.

Figure 6:
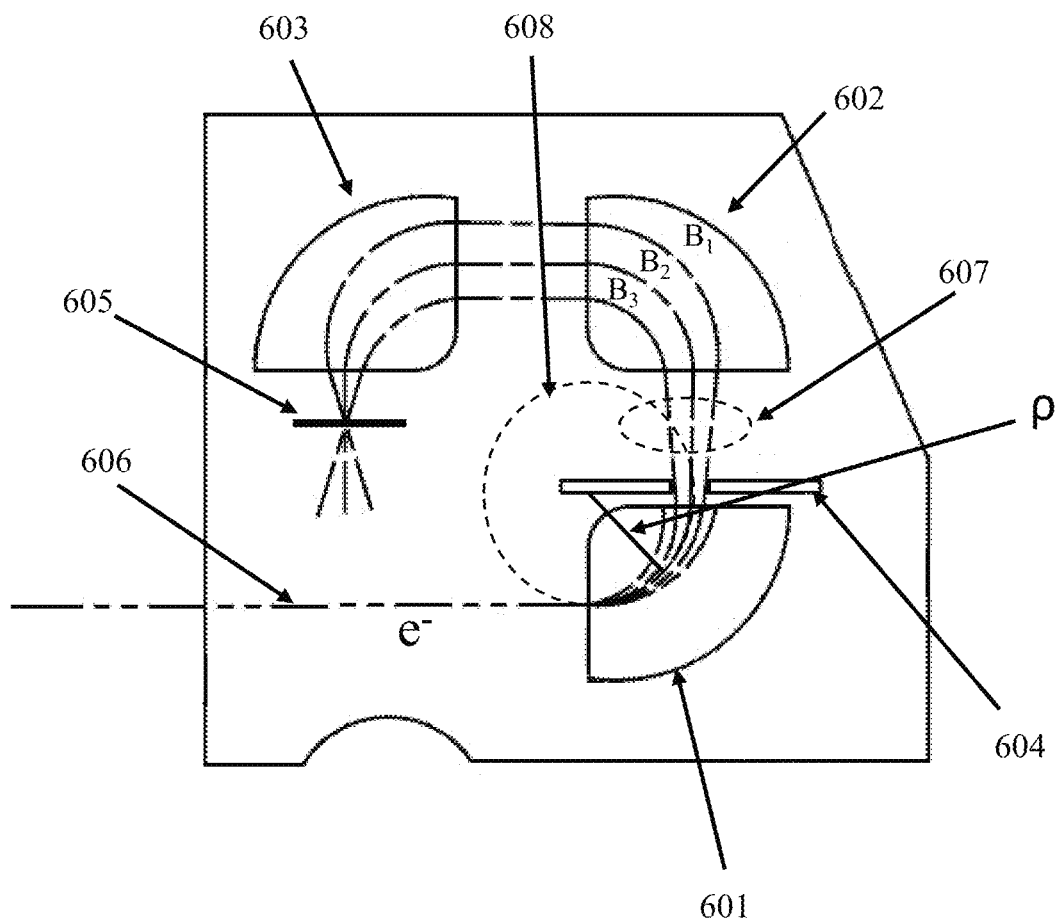
FIG. 6 is a schematic diagram of an exemplary beam deflection device according to some embodiments of the present disclosure.

FIG. 6 is a schematic diagram of an exemplary beam deflection device according to some embodiments of the present disclosure.

As shown in FIG. 6, the beam deflection device 600 may include a first deflecting magnet 601, a second deflecting magnet 602, a third deflecting magnet 603, and an energy slit 604. The first deflecting magnet 601, the second deflecting magnet 602, and the third deflecting magnet 603 may be connected by a drift tube. FIG. 6 shows motion trajectories of electrons having different energies in the beam deflection device 600. The incident electron beam 606 emitted from the accelerating tube 464 may enter the beam deflection device 600, and be deflected after passing through the first deflecting magnet 601. Electrons having different energies in the incident electron beam 606 may have different deflection radius in a magnetic field generated by the first deflecting magnet 601. The first deflecting magnet 601 may generate a magnetic field based on a deflection current. Different magnetic fields may be generated based on different deflection currents. After deflected by the first deflecting magnet 601, electrons in the incident electron beam 606 may be filtered by the energy slit 604.

In some embodiments, the energy slit 604 may be referred to as a power selection mechanism, an energy selection device, or the like. For example, the energy slit 604 may be a panel structure where a slit is located. In some embodiments, the energy slit 604 may be disposed between the first deflecting magnet 601 and the second deflecting magnet 602. The beam deflection device 600 is provided for illustration purposes, and other similar beam deflection device also falls within the scope of protection of the present disclosure. In some embodiments, the slit on the energy slit 604 may have a specific width set at a specific position in the beam deflection device 600. Therefore, only electrons of specific deflection radius under the magnetic field generated by the first deflecting magnet 601 may pass through the energy slit 604, while electrons of other deflection radii (and accordingly of other energies) cannot pass through the energy slit 604.

The electron beam formed by the electrons that pass through the energy slit 604 may be referred to as an ejected electron beam 607. In some embodiments, the beam deflection device 600 may function as an achromatic dispersion for the ejected electron beam 607. For example, as shown in FIG. 6, electrons of different energies in the ejected electron beam 607 may be emitted from the output of the beam deflection device 600 after the deflection of the second deflecting magnet 602 and the third deflecting magnet 603. The electrons in the ejected electron beam 607 may be concentrated on the target 605. The second deflecting magnet 602 may generate a gradient magnetic field, as shown in FIG. 6, which includes different magnetic field strengths B1, B2, B3, etc. When the ejected electron beam 607 reaches on the target 605, the target 605 may be irradiated to generate radiations, for example, X-rays. When the ejected electron beam 607 reaches on the target 605, a target current flowing through the target 605 may be measured by a target current test device (for example, an oscilloscope). The magnitude of the target current and the energy range of the ejected electron beam 607 may reflect the energy spectrum distribution of the ejected electron beam 607.

A center energy value of the ejected electron beam 607 may be E, and the energy range of the ejected electron beam 607 may be [E−ΔE, E+ΔE]. Only electrons whose energies are between [E−ΔE, E+ΔE] may pass through the energy slit 604. A parameter k=ΔE/E may be related to the design of the energy slit 604. In some embodiments, the parameter k may be 3%, 5%, 7%, 10%, etc. For example, when k is 7%, the energy slit 604 may permit electrons whose energies fall within a range with a width of ±7% to pass through. In some embodiments, electrons having energies outside the range (e.g., electrons of other deflection radii) may be blocked by the energy slit 604.

In some embodiments, the beam deflection device 600 may be an electromagnet. The deflection current of the beam deflection device 600 may be set by the one or more terminals 130 to change the magnetic field strength generated by the beam deflection device 600. When the intensity of the magnetic field generated by the beam deflection device 600 changes, the deflection radius of the electrons of the different energies in the incident electron beam 606 may be changed. Under different deflection currents, the energy slit 604 may allow electrons in different specific energy ranges to pass through. Further, at a different deflection current, the ejected electron beam 607 formed by the electrons passing through the energy slit 604 in the incident electron beam 606 may be changed. The energy range of the ejected electron beam 607 may be determined based on the deflection current.

When the deflection current of the beam deflection device 600 is A, the corresponding magnetic field strength of the beam deflection device 600 may be B. In some embodiments, at least the magnetic field of a region including the motion trajectories of the electrons may be maintained to be B. The incident electron beam 606 may be deflected in the magnetic field of the beam deflection device 600, and electrons of different energies may separate. The center energy value of the ejected electron beam 607 may be determined according to a deflection radius ρ of the beam deflection device and the magnetic field strength B. In some embodiments, the deflection radius ρ of the beam deflection device may be determined based on the design of the beam deflection device 600. For example, the deflection radius ρ of the beam deflection device may be determined based on at least one factor of a size of the first deflecting magnet 601, the position of the entrance of the first deflecting magnet 601 through which the incident electron beam enters the first deflecting magnet 601, the position of the energy slit 604, or the size of the energy slit 604. In some embodiments, the position of the entrance of the first deflecting magnet 601 and the position of the center of the energy slit 604 may fall on the circumference of a circle whose radius is the deflection radius ρ of the beam deflection device. The circle may be determined based on an angle of incidence of the incident electron beam, the position of the entrance of the first deflecting magnet 601 and the position of the center of the energy slit 604. The angle of incidence of the incident electron beam may be an angle between the direction of the incident electron beam and a normal of an edge of the first deflecting magnet 601 in a plane perpendicular to the magnetic field in the first deflecting magnet 601. As shown in FIG. 6, the angle of incidence may be 0°, and the circle 608 and the deflection radius ρ of the beam deflection device may be determined based on the position of the entrance of the first deflecting magnet 601 and the position of the center of the energy slit 604. In some embodiments, an arc from the position of the entrance of the first deflecting magnet 601 to the position of the center of the energy slit 604 may be a portion (e.g., a quarter, or another fraction) of the circle. In some embodiments, the center energy value E of the ejected electron beam 607 may be derived from equation (1). For different beam deflection device 600, the coefficients and constants in the following equation (1) may be different.

$$E=0.3*B\rho-0.511 \text{ (MeV)}, \tag{1}$$

where B is the magnetic field strength of the first deflecting magnet 601, and ρ is the deflection radius of the beam deflection device. Based on the design of the energy slit 604, after the incident electron beam 606 is deflected by the beam deflection device 600, the ejected electron beam 607 emitted from the output of the beam deflection device 600 may be the energy range of [E−ΔE, E+ΔE]. Electrons having energy outside the energy range [E−ΔE, E+ΔE] may not pass through the energy slit 604. Where ΔE=k*E and the parameter k may be related to the design of the energy slit 604.

When the parameter k is determined, if the center energy value E of the ejected electron beam 607 becomes larger, the width of the energy range of the ejected electron beam 607 range may be larger. If the center energy value E of the ejected electron beam 607 becomes smaller, the width of the energy range of the ejected electron beam 607 range may be smaller. After the ejected electron beam 607 reaches to the target 605, the target current I flowing through the target 605 may be measured by a target current test device. That is, the deflection current A, the center energy value E of the ejected electron beam 607, the energy range [E−ΔE, E+ΔE] of the ejected electron beam 607, and the target current I may be mutually corresponding.

By gradually changing (e.g., successively reducing or successively increasing) the deflection current of the beam deflection device 600, the energy range of the ejected electron beam 607 emitted from the output of the beam deflection device 600 may be determined, and the target current corresponding to the energy range of the ejected electron beam 607 may also be determined accordingly. Thereby the energy spectrum distribution of the incident electron beam 606 may be determined.

In some embodiments, the deflection current A of the beam deflection device 600 may be changed to obtain a plurality of ejected electron beams 607, and a combination of the energy ranges of the plurality of ejected electron beams 607 may cover the energy range of the incident electron beam 606. In some embodiments, a user (for example, a doctor) may only pay attention to the energy spectrum distribution of partial energy range of the incident electron beam 606, instead of the energy spectrum distribution of the entire energy range of the incident electron beam 606. The energy range of a plurality of ejected electron beams 607 may be obtained by changing the deflection current A. The combination of the energy ranges of the plurality of ejected electron beams 607 may cover the energy range that the user pays attention to. Thereby, the energy spectrum distribution of the energy range that the user is concerned with may be obtained without measuring the entire energy spectrum distribution of the incident electron beam 606. In some embodiments, the energy range of the plurality of the ejected electron beams 607 may be continuously distributed. In some embodiments, a start-point of an energy range of an ejected electron beam may coincide with an end-point of an energy range of another ejected electron beam. By combining a plurality of energy ranges of the plurality of the ejected electron beam 607, each having a corresponding target current, the energy spectrum distribution of a desired energy range may be obtained.

In some embodiments, the energy ranges of the plurality of ejected electron beams 607 may be continuously distributed. For example, a start-point of the energy range of a first ejected electron beam may coincide with an end-point of the energy range of a second ejected electron beam generated prior to the first ejected electron beam. As another example, an end-point of the energy range of a first ejected electron beam may coincide with a start-point of the energy range of a second ejected electron beam generated prior to the first ejected electron beam. The energy spectrum distribution of the incident electron beam 606 may be determined based on the energy range of each ejected electron beam 607 and the corresponding target current value.

In some embodiments, the start-point of the energy range of the ejected electron beam may coincide with an end-point of the energy range of at least one previously generated ejected electron beam. In some embodiments, the end-point of the energy range of the ejected electron beam may coincide with a start-point of the energy range of at least one previously generated ejected electron beam. The energy spectrum distribution of the incident electron beam 606 may be obtained by performing a simple mathematical operation on the target current value to determine target current value corresponding to the continuously distributed energy range. For the simple mathematical operation of the target current value, reference may be made to the description of FIG. 7 below.

In some embodiments, the deflection current A of the beam deflection device 600 may be determined such that the target current corresponding to at least one ejected electron beam is 0. Since the deflection current A may be gradually changed, the target current generated by at least one specific ejected electron beam of the plurality of ejected electron beams irradiating the target may be 0, and each of the plurality of ejected electron beams other than the at least one specific ejected electron beam may meet at least one of the following conditions: (1) the energy range of the each ejected electron beam at least partially overlaps with the energy range of the at least one specific ejected electron beam; and (2) a start-point or an end-point of the energy range of the each ejected electron beam may coincide with a start-point or an end-point of the energy range of any ejected electron beam generated prior to the each ejected electron beam. The energy spectrum distribution of the incident electron beam 606 may be obtained by performing a mathematical operation on the target current value to determine the target current value corresponding to the continuously distributed energy range. Descriptions regarding an applicable mathematical operation of the target current value may be found in FIG. 7 and the description thereof.

Figure 7:
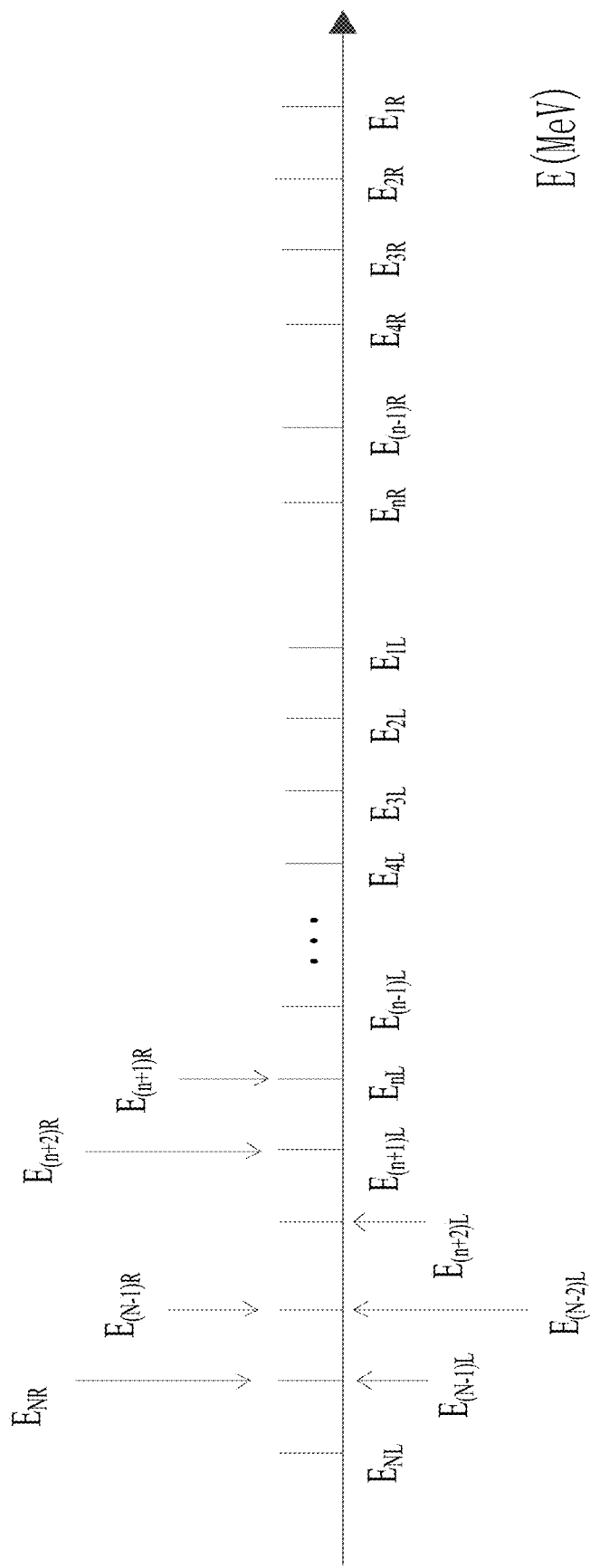
FIG. 7 is a schematic diagram of an exemplary energy range distribution according to some embodiments of the present disclosure.

FIG. 7 is a schematic diagram of an exemplary energy range distribution according to some embodiments of the present disclosure.

The following describes the deflection current A of the beam deflection device 600 as an example, which is not intended to limit the present disclosure.

As shown in FIG. 7, when a first deflection current of the beam deflection device 600 is $A_1$, the energy range of a first ejected electron beam may be $[E_{1L}, E_{1R}]$, and the first target current corresponding to the energy range may be $I_1$.

When a second deflection current of the beam deflection device 600 is changed to $A_2$, the energy range of the second ejected electron beam may be $[E_{2L}, E_{2R}]$, and the second target current corresponding to the energy range may be 12, where $A_2<A_1$ and $E_{2L}<E_{1L}<E_{2R}<E_{1R}$.

In some embodiments, in order to determine a target current corresponding to the energy range $[E_{2L}, E_{1L}]$, the first deflection current $A_1$ of the beam deflection device 600 may be set such that the first target current $I_1=0$. If $I_1=0$, the target current corresponding to the energy range $[E_{1L}, E_{2R}]$ may be 0, and the target current corresponding to the energy range $[E_{2L}, E_{1L}]$ may be $I_2$.

When a third deflection current of the beam deflection device 600 is $A_3$, the energy range of a third ejected electron beam may be $[E_{3L}, E_{3R}]$, and a third target current corresponding to the energy range may be 13, where $A_3<A_2$, and $E_{3L}<E_{2L}<E_{1L}<E_{3R}<E_{2R}<E_{1R}$. Since the target current corresponding to the energy range $[E_{1L}, E_{2R}]$ is 0, the target current corresponding to the energy range $[E_{1L}, E_{3R}]$ may be 0, and the target current corresponding to the energy range $[E_{3L}, E_{2L}]$ may be $I_3-I_2$.

When a fourth deflection current of the beam deflection device 600 is $A_4$, the energy range of a fourth ejected electron beam may be $[E_{4L}, E_{4R}]$, and a fourth target current corresponding to the energy range is $I_4$, where $A_4<A_3$, and $E_{4L}<E_{3L}<E_{2L}<E_{1L}<E_R<E_{3R}<E_{2R}<E_{1R}$. Similarly, the target current corresponding to the energy range $[E_{4L}, E_{3L}]$ may be derived as $I_4-I_3$.

Similarly, when an nth deflection current of the beam deflection device 600 is $A_n$, where n is a positive integer greater than 1, the energy range of an nth ejected electron beam may be $[E_{nL}, E_{nR}]$, and an nth target current corresponding to the energy range may be $I_n$. If $E_{nR}>E_{1L}$, then the target current corresponding to the energy range $[E_{nL}, E_{(n-1)L}]$ may be $I_n-I_{n-1}$.

When an (n+1)th deflection current is $A_{n+1}$, the energy range of an (n+1)th ejected electron beam may be $[E_{(n+1)L}, E_{(n+1)R}]$, and an (n+1)th target current corresponding to the energy range may be $I_n$. If $E_{(n+1)R}<E_{1L}$, then an appropriate $A_{n+1}$ may be determined such that $E_{(n+1)R}=E_{nL}$, then $[E_{(n+1)L}, E_{(n+1)R}]=[E_{(n+1)L}, E_{nL}]$, and the target current corresponding to energy range $[E_{(n+1)L}, E_{nL}]$ may be $I_{n+1}$.

When an (n+2)th deflection current is $A_{n+2}$, the energy range of an (n+2)th ejected electron beam may be $[E_{(n+2)L}, E_{(n+2)R}]$, and an (n+2)th target current corresponding to the energy range may be $I_{n+2}$. By setting an appropriate $A_{n+2}$ to get $E_{(n+2)R}=E_{(n+1)L}$, then $[E_{(n+2)L}, E_{(n+2)R}]=[E_{(n+2)L}, E_{(n+1)L}]$, and the target current corresponding to the energy range $[E_{(n+2)L}, E_{(n+1)L}]$ may be $I_{n+2}$.

Similarly, when an (N−1)th deflection current is $A_{N-1}$, where N is a positive integer greater than n, and the energy range of an (N−1)th ejected electron beam may be $[E_{(N-1)L}, E_{(N-1)R}]$, and an (N−1)th target current corresponding to the energy range may be $I_{N-1}$. By setting an appropriate $A_{N-1}$ to get $E_{(N-1)R}=E_{(N-2)L}$, then $[E_{(N-1)L}, E_{(N-1)R}]=[E_{(N-1)L}, E_{(N-2)L}]$, and the target current corresponding to the energy range $[E_{(N-1)L}, E_{(N-2)L}]$ may be $I_{N-1}$.

When an Nth deflection current is $A_N$, the energy range of an Nth ejected electron beam may be $[E_{NL}, E_{NR}]$, and an Nth target current corresponding to the energy range may be $I_N$. By setting an appropriate $A_N$ to get $E_{NR}=E_{(N-1)L}$, then energy range $[E_{NL}, E_{NR}]=[E_{NL}, E_{(N-1)L}]$, and the target current corresponding to energy range $[E_{NL}, E_{(N-1)L}]$ may be $I_N$. In some embodiments, $I_N=0$ may be determined as the end condition, i.e., the Nth deflection current $A_N$ may be the last deflection current. In some embodiments, $A_1$, $A_2$, $A_3$, ..., $A_n$, $A_{n+1}$, $A_{n+2}$, ..., $A_{N-1}$, $A_N$ may be sequentially reduced in order.

As described above, energy range of the incident electron beam 606 emitted from the accelerating tube may be divided into a plurality of energy sub-ranges including $[E_{2L}, E_{1L}]$, $[E_{3L}, E_{2L}]$, $[E_{4L}, E_{3L}]$, ..., $[E_{nL}, E_{(n-1)L}]$, $[E_{(n+1)L}, E_{nL}]$, ..., $[E_{(N-1)L}, E_{(N-2)L}]$. The target current value corresponding to each energy sub-range may be determined, thereby obtaining an energy spectrum distribution of the incident electron beam 606. As the deflection current decreases, the width of the energy range of the ejected electron beam 607 emitted from the output of the beam deflection device 600 may also decrease. In order to obtain a highly accurate energy spectrum distribution, the step size for reducing the deflection current may be chosen to be relatively small. Therefore, the energy range of the incident electron beam 606 may be relatively finely divided, thereby finally obtaining a highly accurate energy spectrum.

The energy spectrum of the incident electron beam 606 may be obtained by determining the target current corresponding to different energy sub-ranges. Table 1 shows the relationship between different energy sub-ranges and the corresponding target current. As shown in Table 1, the target current corresponding to the energy sub-range $[E_{2L}, E_{1L}]$ may be $I_2$, the target current corresponding to the energy sub-range $[E_{3L}, E_{2L}]$ may be $I_3-I_2$, the target current corresponding to the energy sub-range $[E_{4L}, E_{3L}]$ may be $I_4-I_3$, ..., the target current corresponding to the energy sub-range $[E_{nL}, E_{(n-1)L}]$ may be $I_n-I_{n-1}$, the target current corresponding to the energy sub-range $[E_{(n+1)L}, E_{nL}]$ may be $I_{n+1}$, ..., the target current corresponding to the energy sub-range $[E_{(N-1)L}, E_{(N-2)L}]$ may be $I_{N-1}$. And the energy spectrum of the incident electron beam 606 may be determined based on the target currents corresponding to the plurality of the energy sub-ranges.

TABLE 1

Relationship between the energy sub-range of the incident electron beam and the corresponding target current

| Condition | Energy subrange | target current |
|---|---|---|
| $E_{nR}>E_{1L}$ | $[E_{1L}, \infty]$ | $I_1=0$ |
| | $[E_{2L}, E_{1L}]$ | $I_2$ |
| | $[E_{3L}, E_{2L}]$ | $I_3-I_2$ |
| | $[E_{4L}, E_{3L}]$ | $I_4-I_3$ |
| | ... | ... |
| | $[E_{nL}, E_{(n-1)L}]$ | $I_n-I_{n-1}$ |
| $E_{(n+1)R}<E_{1L}$ | $[E_{(n+1)L}, E_{nL}]$ | $I_{n+1}$ |
| | $[E_{(n+2)L}, E_{(n+1)L}]$ | $I_{n+2}$ |
| | ... | ... |
| | $[E_{(N-1)L}, E_{(N-2)L}]$ | $I_{N-1}$ |

In some embodiments, when $E_{(n+1)R} \leq E_{1L}$, an appropriate $A_{n+1}$ may also be determined such that $E_{(n+1)R}=E_{jL}$, where $j=1, 2, 3, ..., n-1$, then $[E_{(n+1)L}, E_{(n+1)R}]=[E_{(n+1)L}, E_{jL}]$, then energy range $[E_{(n+1)L}, E_{nL}]=[E_{(n+1)L}, E_{jL}]-\{[E_{nL}, E_{(n-1)L}]+...+[E_{(j+1)L}, E_{jL}]\}$. Since the target currents corresponding to the energy ranges $[E_{(n+1)L}, E_{jL}]$, $[E_{nL}, E_{(n-1)L}]$, ..., $[E_{(j+1)L}, E_{jL}]$ are known, range the target current value corresponding to energy range $[E_{(n+1)L}, E_{nL}]$ may be determined accordingly.

Figure 8:
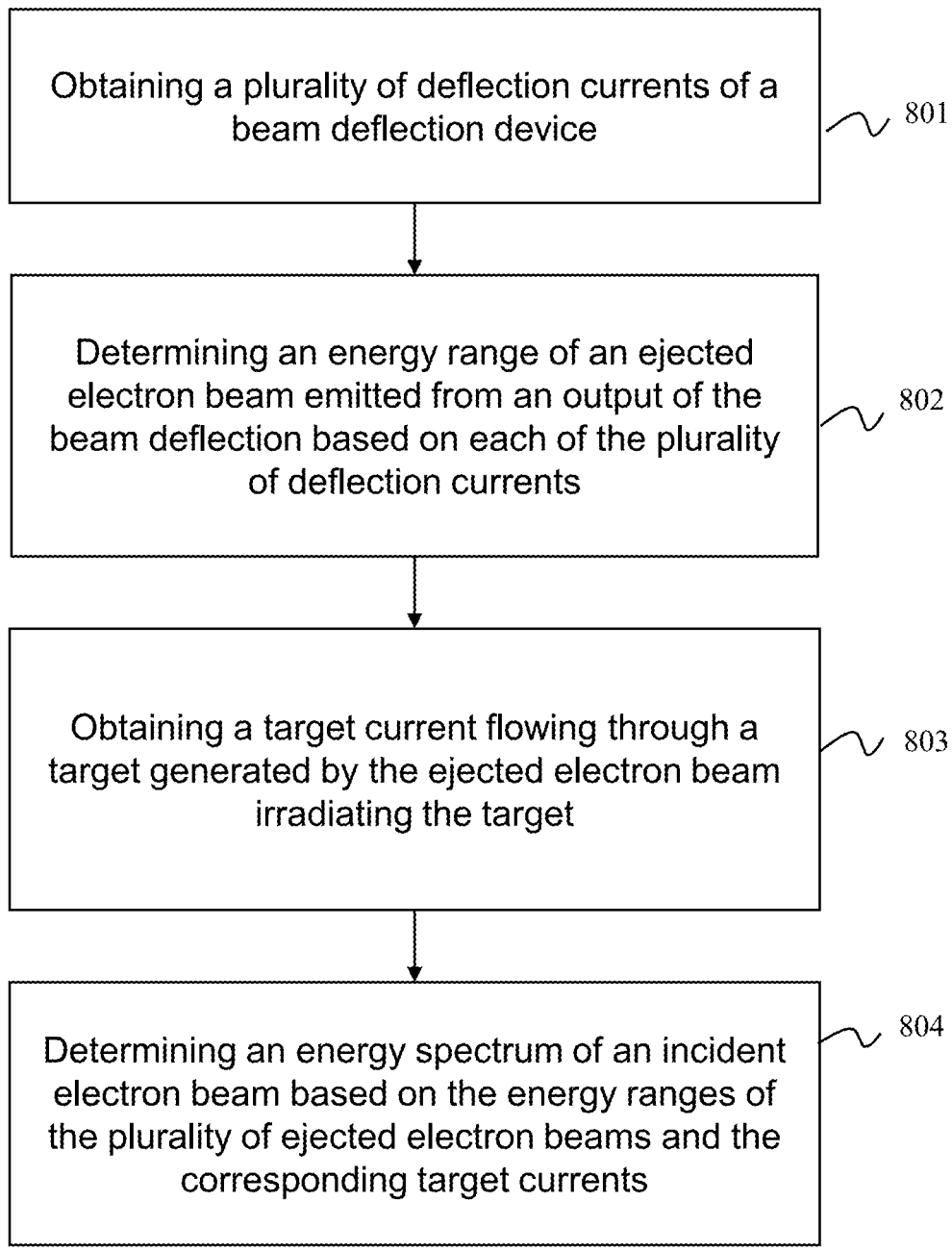
FIG. 8 is a flowchart of an exemplary process for determining an energy spectrum of an electron beam according to some embodiments of the present disclosure.

FIG. 8 is a flowchart of an exemplary process for determining an electron beam energy spectrum according to some embodiments of the present disclosure.

The process 800 may be performed by the processing device 140. The processing device 140 may include hardware (e.g., circuitry, dedicated logic, programmable logic, microcode, etc.), software (instructions that executed by the processing device 140), or the like, or any combination thereof. For the ease of description, the process 800 is described in conjunction with the contents of FIG. 6 and FIG. 7.

In 801, the processing device 140 may obtain a plurality of deflection currents of the beam deflection device.

As shown in FIG. 7, the processing device 140 may obtain a plurality of deflection currents, e.g., $A_1, A_2, A_3, \ldots, A_n, A_{n+1}, A_{n+2}, \ldots, A_{N-1}, A_N$. Where N may be a positive integer and n may be a positive integer that is less than N. For the purpose of illustration only, $A_1, A_2, A_3, \ldots, A_n, A_{n+1}, A_{n+2}, \ldots, A_{N-1}, A_N$ may be in a decreasing order. The beam deflection device may be the beam deflection device described in FIG. 6.

In 802, the processing device 140 may determine an energy range of an ejected electron beam based on each of the plurality of deflection currents. The ejected electron beam may be formed by electrons emitted from the output end of the beam deflection device after the incident electron beam enters the beam deflection device.

In some implementations, the incident electron beam may be the electron beam that is accelerated in an accelerating tube. Taking the deflection current as $A_1$ as an example, the processing device 140 may determine a magnetic field strength $B_1$ of the beam deflection device based on the deflection current $A_1$. Electrons of the incident electron beam may be deflected in the magnetic field generated based on the deflection current $A_1$. Electrons having different energies may have different deflection radii in the same magnetic field generated based on the deflection current $A_1$.

The processing device 140 may also determine a center energy value $E_1$ of the energy range of the ejected electron beam according to the deflection radius $\rho$ and the magnetic field strength $B_1$. According to equation (1), the center energy value of the ejected electron beam $E_1 = 0.3 * B_1 \rho - 0.511$ (MeV) may be obtained.

Further, the processing device 140 may determine an energy range of the ejected electron beam based on the center energy value $E_1$ and a width of the energy range of the ejected electron beam. The width of the energy range may be determined based on the design of the energy slit 604. For example, the energy range corresponding to the ejected electron beam may be $[E_{1L}, E_{1R}] = [E_1 - \Delta E_1, E_1 + \Delta E_1]$, where $\Delta E_1 = k * E_1$. The energy range may be $2\Delta E_1$. The parameter k may be related to the design of the energy slit in the beam deflection device. For example, k is 7%, indicating that the energy slit may permit electrons whose energies fall within a range with the width of ±7% to pass through.

Similarly, when the deflection current is $A_2$, the energy range corresponding to the ejected electron beam may be $[E_{2L}, E_{2R}] = [E_2 - \Delta E_2, E_2 + \Delta E_2]$, where $\Delta E_2 = k * E_2$. When the deflection current is $A_3$, the energy range corresponding to the ejected electron beam may be $[E_{3L}, E_{3R}] = [E_3 - \Delta E_3, E_3 + \Delta E_3]$, where $\Delta E_3 = k * E_3$.

When the deflection current is $A_n$, the energy range corresponding to the nth ejected electron beam may be $[E_{nL}, E_{nR}] = [E_n - \Delta E_n, E_n + \Delta E_n]$, where $\Delta E_n = k * E_n$. In some embodiments, the condition $E_{nR} > E_{1L}$ may need to be satisfied.

In some embodiments, when $E_{(n+1)R} < E_{1L}$, and the deflection current is $A_{n+1}$, the energy range corresponding to the (n+1)th ejected electron beam may be $[E_{(n+1)L}, E_{(n+1)R}] = [E_{(n+1)} - \Delta E_{(n+1)}, E_{(n+1)} + \Delta E_{(n+1)}]$, where $\Delta E_{n+1} = k * E_{n+1}$. In some embodiments, the condition $E_{(n+1)R} = E_{nL}$ may need to be satisfied.

Similarly, when the deflection current is $A_{n+2}$, the energy range corresponding to the (n+2)th ejected electron beam may be $[E_{(n+2)L}, E_{(n+2)R}] = [E_{(n+2)} - \Delta E_{(n+2)}, E_{(n+2)} + \Delta E_{(n+2)}]$, where $\Delta E_n + 2 = k * E_n + 2$. In some embodiments, the condition $E_{(n+2)R} = E_{(n+1)L}$ may need to be satisfied.

When the deflection current is $A_{N-1}$, the energy range corresponding to the N−1th ejected electron beam may be $[E_{(N-1)L}, E_{(N-1)R}] = [E_{(N-1)} - \Delta E_{(N-1)}, E_{(N-1)} + \Delta E_{(N-1)}]$, where $\Delta E_{N-1} = k * E_{N-1}$. In some embodiments, the condition $E_{(N-1)R} = E_{(N-2)L}$ may need to be satisfied.

When the deflection current is $A_N$, the energy range corresponding to the Nth ejected electron beam may be $[E_{NL}, E_{NR}] = [E_N - \Delta E_N, E_N + \Delta E_N]$, where $\Delta E_N = k * E_N$. In some embodiments, the condition $E_{NR} = E_{(N-1)L}$ may need to be satisfied. N may be a positive integer.

According to the above process, the processing device 140 may determine the intensity of the magnetic field generated by the beam deflection device based on each deflection current. The processing device 140 may also determine the center energy value of the energy range of each ejected electron beam based on the magnetic field strength generated by the beam deflection device and the deflection radius. Further, the processing device 140 may determine the energy range of each of the ejected electron beams based on the center energy value and the width of the energy range of each of the plurality of ejected electron beams.

In 803, the processing device 140 may obtain a target current flowing through a target after each of the plurality of ejected electron beams irradiates the target. The target may be configured to generate radiations.

The processing device 140 may obtain the target current corresponding to the energy range of each ejected electron beam. For example, the processing device may obtain the first ejected electron beam whose energy range is $[E_{1L}, E_{1R}]$, and the target current may be $I_1$. Similarly, the energy range of the second ejected electron beam is $[E_{2L}, E_{2R}]$, and the corresponding target current may be $I_2$. The energy range of the third ejected electron beam is $[E_{3L}, E_{3R}]$, and the corresponding target current may be $I_3$. The energy range of the nth ejected electron beam is $[E_{nL}, E_{nR}]$, and the corresponding target current may be $I_n$. The energy range of the (n+1)th ejected electron beam is $[E_{(n+1)L}, E_{(n+1)R}]$, and the corresponding target current may be $I_{n+1}$. The energy range of the (n+2)th ejected electron beam is $[E_{(n+2)L}, E_{(n+2)R}]$, and the corresponding target current may be $I_{n+2}$. The energy range of the N−1th ejected electron beam is $[E_{(N-1)L}, E_{(N-1)R}]$, and the corresponding target current may be $I_{N-1}$. The energy range of the Nth ejected electron beam is $[E_{NL}, E_{NR}]$, and the corresponding target current may be $I_N$.

In 804, the processing device 140 may determine an energy spectrum of the incident electron beam based on the energy ranges of the plurality of ejected electron beams and the plurality of target currents corresponding to the plurality of ejected electron beams.

Specifically, the processing device 140 may divide the energy range of the incident electron beam into a plurality of energy sub-ranges based on the energy range of the plurality of ejected electron beams.

As shown in FIG. 7, the processing device 140 may divide the energy range of the incident electron beam into a plurality of energy sub-ranges. For example, the plurality of energy sub-ranges may include $[E_{2L}, E_{1L}], [E_{3L}, E_{2L}], [E_{4L}, E_{3L}], \ldots, [E_{nL}, E_{(n-1)L}], [E_{(n+1)L}, E_{nL}], \ldots, [E_{(N-1)L}, E_{(N-2)L}]$.

The processing device 140 may determine a sub-current corresponding to each energy sub-range based on the target currents corresponding to the energy range of the plurality of ejected electron beams.

As shown in FIG. 7, when the deflection current of the beam deflection device is $A_1$, the energy range of the ejected electron beam may be $[E_{1L}, E_{1R}]$, and the target current corresponding to the energy range may be $I_1$.

When the deflection current of the beam deflection device is $A_2$, the energy range of the ejected electron beam may be $[E_{2L}, E_{2R}]$, and the target current corresponding to the energy range may be $I_2$, where $A_2 < A_1$ and $E_{2L} < E_{1L} < E_{2R} < E_{1R}$.

In some embodiments, in order to determine the target current corresponding to the energy range $[E_{2L}, E_{1L}]$, the deflection current $A_1$ of the beam deflection device may be controlled such that the corresponding target current $I_1 = 0$. If $I_1 = 0$, the sub-current corresponding to the energy sub-range $[E_{1L}, E_{2R}]$ may be 0, and the sub-current corresponding to the energy sub-range $[E_{2L}, E_{1L}]$ may be $I_2$.

When the deflection current of the beam deflection device is $A_3$, the energy range of the ejected electron beam may be $[E_{3L}, E_{3R}]$, and the target current corresponding to the energy range may be $I_3$, where $A_3 < A_2$, and $E_{3L} < E_{2L} < E_{1L} < E_{3R} < E_{2R} < E_{1R}$. Since the current corresponding to the energy range $[E_{1L}, E_{2R}]$ is 0, the target current corresponding to the energy range $[E_{1L}, E_{3R}]$ may be 0, and the sub-current corresponding to the energy sub-range $[E_{3L}, E_{2L}]$ may be $I_3 - I_2$.

When the deflection current of the beam deflection device is $A_4$, the energy range of the ejected electron beam may be $[E_{4L}, E_{4R}]$, and the target current corresponding to the energy range may be 14, where $A_4 < A_3$, and $E_{4L} < E_{3L} < E_{2L} < E_{1L} < E_R < E_{3R} < E_{2R} < E_{1R}$. Similarly, the sub-current corresponding to the energy sub-range $[E_{4L}, E_{3L}]$ may be derived as $I_4 - I_3$.

Similarly, when the deflection current of the beam deflection device is $A_n$, where n is a positive integer greater than 1, the energy range of the ejected electron beam may be $[E_{nL}, E_{nR}]$, and the target current corresponding to the energy range is $I_n$. If $E_{nR} > E_{1L}$, the sub-current corresponding to the energy sub-range $[E_{nL}, E_{(n-1)L}]$ may be obtained as $I_n - I_{n-1}$.

When the deflection current is $A_{n+1}$, the energy range of the ejected electron beam may be $[E_{(n+1)L}, E_{(n+1)R}]$, and the target current corresponding to the energy range may be $I_{n+1}$. If $E_{(n+1)R} < E_{1L}$, then an appropriate $A_{n+1}$ may be determined such that $E_{(n+1)R} = E_{nL}$, and $[E_{(n+1)L}, E_{(n+1)R}] = [E_{(n+1)L}, E_{nL}]$. The sub-current corresponding to energy sub-range $[E_{(n+1)L}, E_{nL}]$ may be $I_{n+1}$.

When the deflection current is $A_{n+2}$, the energy range of the ejected electron beam may be $[E_{(n+2)L}, E_{(n+2)R}]$, and the target current corresponding to the energy range may be $I_{n+2}$. By setting an appropriate $A_{n+2}$ to get $E_{(n+2)R} = E_{(n+1)L}$, then $[E_{(n+2)L}, E_{(n+2)R}] = [E_{(n+2)L}, E_{(n+1)L}]$. The sub-current corresponding to the energy sub-range $[E_{(n+2)L}, E_{(n+1)L}]$ may be $I_{n+2}$.

Similarly, when the deflection current is $A_{N-1}$, where N is a positive integer greater than n, the energy range of the ejected electron beam may be $[E_{(N-1)L}, E_{(N-1)R}]$, and the target current corresponding to the energy range may be $I_{N-1}$. By setting an appropriate $A_{N-1}$ to get $E_{(N-1)R} = E_{(N-2)L}$, then $[E_{(N-1)L}, E_{(N-1)R}] = [E_{(N-1)L}, E_{(N-2)L}]$. The sub-current corresponding to the energy sub-range $[E_{(N-1)L}, E_{(N-2)L}]$ may be $I_{N-1}$.

When the deflection current is $A_N$, the energy range of the Nth ejected electron beam is $[E_{NL}, E_{NR}]$, and the target current corresponding to the energy range may be $I_N$. By setting an appropriate $A_N$ to get $E_{NR} = E_{(N-1)L}$, then energy range $[E_{NL}, E_{NR}] = [E_{NL}, E_{(N-1)L}]$. The sub-current corresponding to energy sub-range $[E_{NL}, E_{(N-1)L}]$ may be $I_N$. In some embodiments, $I_N = 0$ may be determined as the end condition. For example, deflection current $A_N$ is the last deflection current. In some embodiments, the magnitudes of the deflection currents $A_1, A_2, A_3, \ldots, A_n, A_{n+1}, A_{n+2}, \ldots, A_{N-1}, A_n$ may be in a descending order.

In some embodiments, when $E_{(n+1)R} \leq E_{1L}$, an appropriate $A_{n+1}$ may also be determined such that $E_{(n+1)R} = E_{jL}$, where $j = 1, 2, 3, \ldots, n-1$. Then $[E_{(n+1)L}, E_{(n+1)R}] = [E_{(n+1)L}, E_{jL}]$. The energy sub-range $[E_{(n+1)L}, E_{nL}] = [E_{(n+1)L}, E_{jL}] - \{[E_{nL}, E_{(n-1)L}] + \ldots + [E_{(j+1)L}, E_{jL}]\}$. Since the sub-currents corresponding to the energy range $[E_{(n+1)L}, E_{jL}]$, $[E_{nL}, E_{(n-1)L}], \ldots, [E_{(j+1)L}, E_{jL}]$ are known, the sub-current value corresponding to energy sub-range $[E_{(n+1)L}, E_{nL}]$ may be determined accordingly.

Further, the processing device 140 may determine an energy spectrum of the incident electron beam based on the sub-current corresponding to each energy sub-range.

Figure 9:
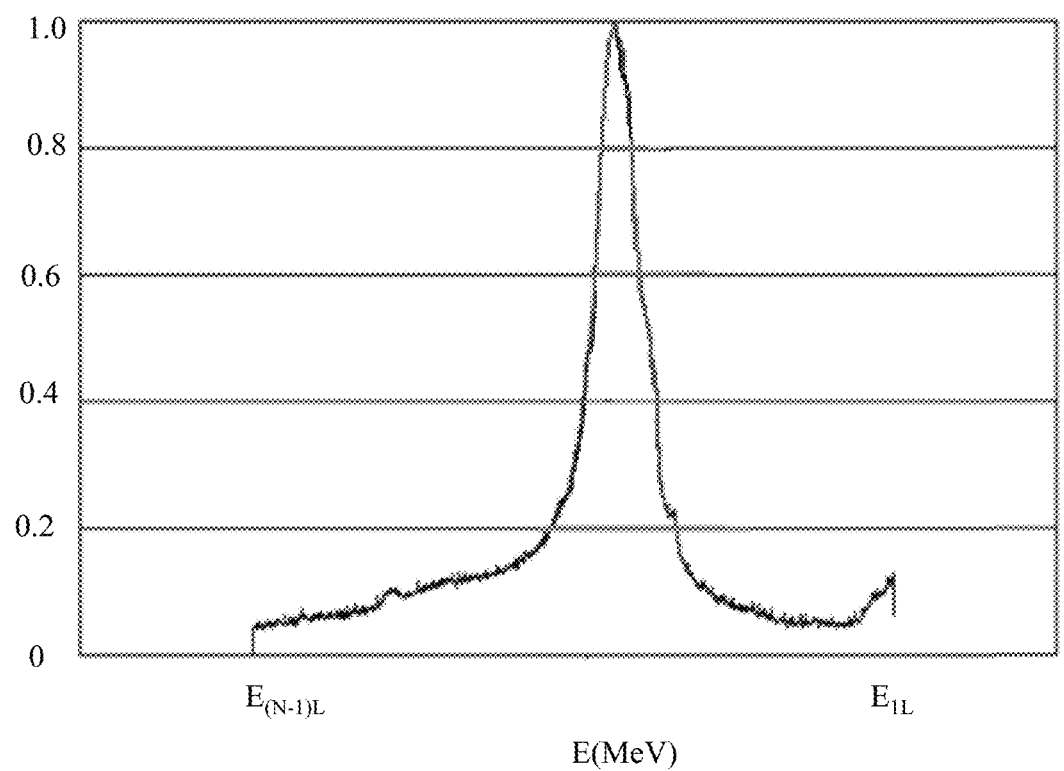
FIG. 9 is a diagram showing an exemplary energy spectrum distribution of an electron beam emitted from an accelerating tube according to some embodiments of the present disclosure.

The processing device 140 may determine an energy spectrum of the incident electron beam based on the sub-current corresponding to each of the energy sub-ranges. As shown in FIG. 9, the horizontal axis may represent the energy sub-ranges distribution of the incident electron beam, and the vertical axis may represent the sub-currents corresponding to the energy sub-ranges. The sub-current represented by the vertical axis may be a normalized sub-current value, instead of an actual sub-current value.

According to the present disclosure, there is no need to insert an energy spectrum analytical device into the accelerating tube system for determining the energy spectrum of an electron beam. Instead, a plurality of energy ranges of the electron beam emitted from the beam deflection device and the corresponding target currents may be obtained by changing the deflection current of the beam deflection device. Thereby, the energy spectrum information of the electron beam emitted from the accelerating tube may be derived.

It is to be noted that the embodiments described in FIG. 8 are merely illustrative and are not intended to limit the scope of the present disclosure. In some embodiments, the energy ranges of the plurality of electron beams corresponding to the deflection currents $A_1, A_2, A_3, \ldots, A_n, A_{n+1}, A_{n+2}, \ldots, A_{N-1}, A_N$ may be continuously distributed, that is, a start-point of an energy range of an ejected electron beam may be an end-point of an energy range of a previous generated ejected electron beam. Based on the energy range of each ejected electron beam and the corresponding target current value, the energy spectrum distribution of the incident electron beam may also be determined.

In some embodiments, one of the start-point and the end-point of the energy range of any ejected electron beams coincides with the start-point or the end-point of the energy range of at least one previously generated ejected electron beam. The energy spectrum distribution of the incident electron beam may also be obtained based on the target current value corresponding to the continuously distributed energy range. Descriptions may refer to FIG. 7.

Figure 10:
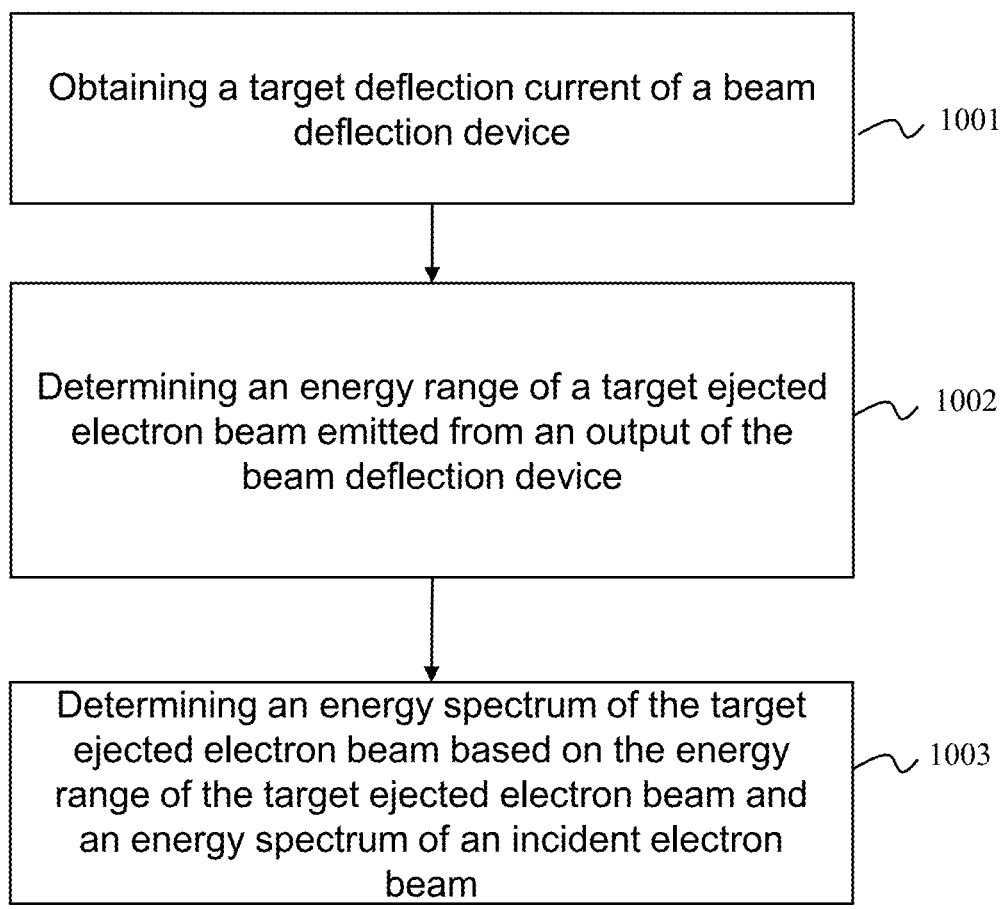
FIG. 10 is a flowchart of an exemplary process for determining an energy spectrum of an electron beam emitted from an output of a beam deflection device according to some embodiments of the present disclosure.

FIG. 10 is a flowchart of an exemplary process for determining an energy spectrum of an electron beam emitted from the output of a beam deflection device according to some embodiments of the present disclosure.

The process 1000 may be performed by the processing device 140. The processing device 140 may include the hardware (e.g., circuitry, dedicated logic, programmable logic, microcode, etc.), the software (instructions that may be executed on the processing device 140), or the like, or any combination thereof.

In 1001, the processing device 140 may obtain a target deflection current of the beam deflection device.

The processing device 140 may obtain the target deflection current $A_0$ of the beam deflection device via the network 120, and the target deflection current $A_0$ may be set by a user through the one or more terminals 130.

In 1002, the processing device 140 may determine an energy range of a target ejected electron beam emitted from the output of the beam deflection device after the incident electron beam enters the beam deflection device. The target ejected electron beam may be formed by the electrons passing through the energy slit and emitted from the output of the beam deflection device. The target ejected electron beam may be a part of the incident electron beam with a specific energy range.

The processing device 140 may determine a magnetic field strength $B_0$ generated by the beam deflection device based on the target deflection current $A_0$. The processing device 140 may determine a center energy value $E_0$ of the energy range of the target ejected electron beam according to the deflection radius $\rho$ and the magnetic field strength $B_0$. According to equation (1), the center energy value of the target ejected electron beam $E_0=0.3*B_0\rho-0.511$ (MeV) may be obtained.

Further, the processing device 140 may determine the energy range of the target ejected electron beam based on the center energy value $E_0$ and the width of the energy range of the target ejected electron beam. Based on the design of the energy slit, the energy range corresponding to the target ejected electron beam may be $[E_a, E_b]=[E_0-\Delta E_0, E_0+\Delta E_0]$, where $\Delta E_0=k*E_0$. The width of the energy range may be $2\Delta E_0$.

In 1003, the processing device 140 may determine the energy spectrum of the target ejected electron beam based on the energy range of the target ejected electron beam and the energy spectrum of the incident electron beam.

Figure 11:
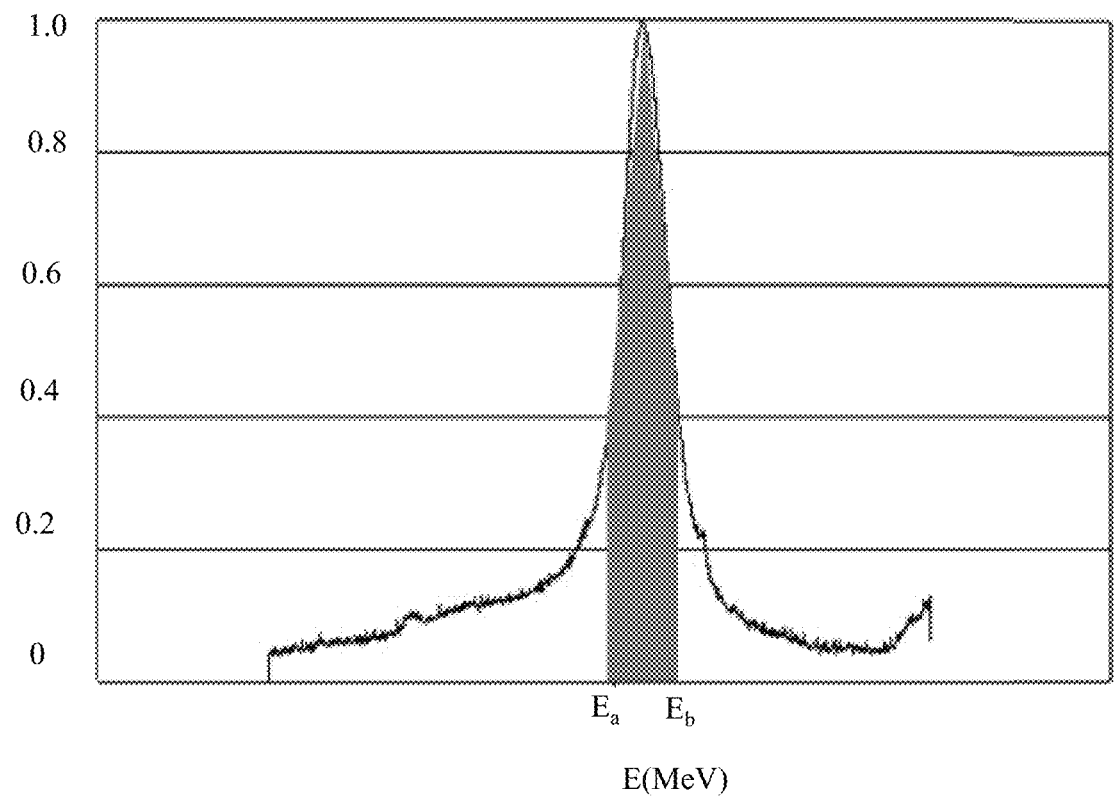
FIG. 11 is a diagram showing an exemplary energy spectrum distribution of an electron beam emitted from an output of a beam deflection device according to some embodiments of the present disclosure.

The processing device 140 may determine the energy spectrum distribution corresponding to the energy range $[E_a, E_b]$ from the energy spectrum distribution (as shown in FIG. 9) of the incident electron beam based on the energy range of the target ejected electron beam, as the gray part shown in FIG. 11.

In some embodiments, the deflection current may be set by a user via the one or more terminals 130. Based on a known energy spectrum information of an electron beam (as shown in FIG. 9) emitted from an accelerating tube, the energy spectrum distribution of an electron beam emitted from the output of the beam deflection device may be obtained.

Figure 12:
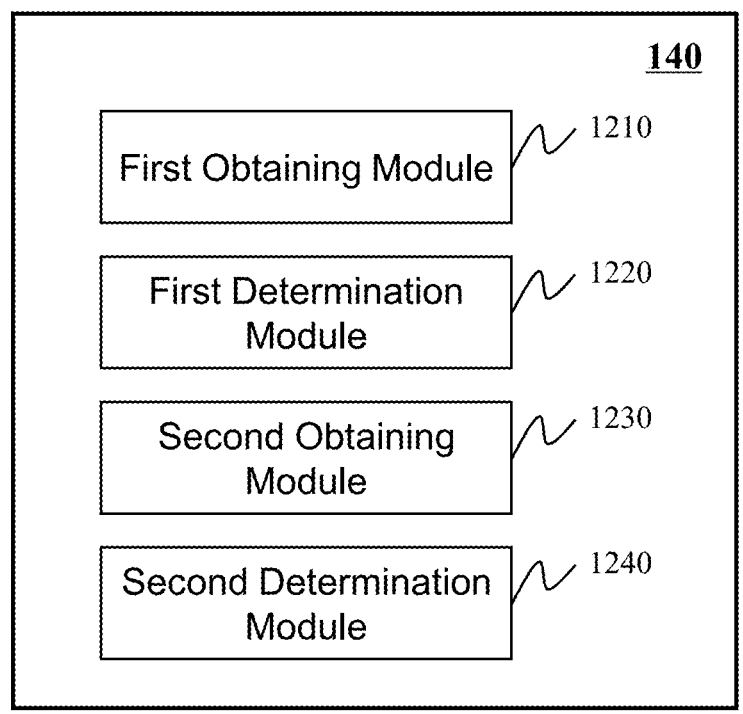
FIG. 12 is a block diagram of an exemplary processing device according to some embodiments of the present disclosure.

FIG. 12 is a block diagram of an exemplary processing device according to some embodiments of the present disclosure.

The processing device 140 may include a first obtaining module 1210, a first determination module 1220, a second obtaining module 1230, and a second determination module 1240.

The first obtaining module 1210 may be configured to obtain a plurality of deflection currents of the beam deflection device.

The first determination module 1220 may be configured to obtain the target current flowing through the target after each of the plurality of ejected electron beams irradiates the target. The target may be configured to generate radiations by being irradiated by the ejected electron beam. In some embodiments, the incident electron beam may be the electron beam accelerated by the accelerating tube.

In some embodiments, the first determination module 1220 may be configured to determine magnetic field strength generated by the beam deflection device based on each deflection current.

In some embodiments, the first determination module 1220 may be configured to determine the center energy value of the energy range of each ejected electron beam based on the plurality of magnetic field strengths and the deflection radius generated by the beam deflection device.

In some embodiments, the first determination module 1220 may be configured to determine an energy range of each of the ejected electron beams based on the center energy value and the width of the energy range of each of the plurality of ejected electron beams.

In some embodiments, the second obtaining module 1230 may be configured to obtain the target current flowing through the target after each of the plurality of ejected electron beams irradiates the target. The target may be used to generate radiations by irradiated by each of the plurality of ejected electron beams.

The second determination module 1240 may be configured to determine the energy spectrum of the incident electron beam based on the energy ranges of the plurality of ejected electron beams and the plurality of target currents corresponding to the plurality of the ejected electron beams.

In some embodiments, the second determination module 1240 may be configured to divide the energy range of the incident electron beam into a plurality of energy sub-ranges based on the energy range of the plurality of ejected electron beams.

The second determination module 1240 may be configured to determine sub-current of each energy sub-range based on the target current corresponding to the energy ranges of the plurality of ejected electron beams.

In some embodiments, the second determination module 1240 may be configured to determine the energy spectrum of the incident electron beam based on the sub-current of each energy sub-range.

In some embodiments, the first obtaining module 1210 may be configured to obtain a deflection current of the beam deflection device.

In some embodiments, the first determination module 1220 may be configured to determine an energy range of a target ejected electron beam emitted from the output of the beam deflection device after the incident electron beam enters the beam deflection device based on the deflection current.

In some embodiments, the second determination module 1240 may be configured to determine an energy spectrum of the target ejected electron beam based on the energy range of the target ejected electron beam and the energy spectrum of the incident electron beam.

It should be understood that the modules shown in FIG. 12 may be implemented in a variety of ways. For example, in some embodiments, the modules may be implemented by the hardware, the software or a combination of the software and the hardware. The hardware may be implemented using specific logic circuits. The software may be stored in memory and executed by an appropriate instruction execution device, such as a microprocessor or a specifically designed hardware. Those skilled in the art may understand that the process and system above may be implemented by executable instructions of a computer and/or control codes in a processor, for example, the code supplied in a carrier medium such as a disk, a CD, a DVD-ROM, a programmable storage such as a read-only memory (firmware), or a data carrier such as an optical signal carrier or an electric signal carrier. The system and its modules of the present disclosure may be implemented by the hardware circuits, e.g., large scale integrated circuits or gate arrays, semiconductors such as logic chips or transistors, programmable hardware devices such as field-programmable gate arrays or programmable logic devices, etc. The system and its modules may be implemented by the software executed by various processors. The system and its modules may also be implemented by a combination (e.g., firmware) of the hardware circuits and the software.

The present disclosure and/or some other examples have been described in the above. According to descriptions above, various alterations may be achieved. The present disclosure may be achieved in various forms and embodiments, and the present disclosure may be further used in a variety of application programs. All applications, modifications and alterations required to be protected in the claims may be within the protection scope of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, certain features, structures, or characteristics of one or more embodiments of the present disclosure may be combined as appropriate.

It may be understood to those skilled in the art that various alterations and improvements may be achieved according to some embodiments of the present disclosure. For example, the various components of the system described above are all achieved by hardware equipment. For example, the system may be installed on the existing server. In addition, the provision of the location information disclosed herein may be achieved by the firmware, a combination of the firmware/software, a combination of the firmware/hardware, or a combination of the hardware/firmware/software.

All or portions of the software may at times be communicated through a network such as the Internet or various other telecommunication networks. Such communications may load the software from one computer device or processor to another. For example: loading from a management server or host computer of a radiation therapy system to a hardware platform of a computer environment, or other computer environment implementing a system, or a system similar to the function that provides the information needed for vertebral recognition and naming. Correspondingly, another media used to transmit software elements may be used as physical connections among some of the equipment. For example, light wave, electric wave, electromagnetic wave, etc. may be transmitted by cables, optical cables or air. Physical media used to carry waves, e.g. cable, wireless connection, optical cable, or the like, may also be considered as media of hosting software. Herein, unless the tangible "storage" media is particularly designated, other terminologies representing the "readable media" of a computer or a machine may represent media joined by the processor when executing any instruction.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python, or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. However, this disclosure does not mean that the present disclosure object requires more features than the features mentioned in the claims. Rather, claim subject matter lie in less than all features of a single rich disclosure.

In some embodiments, the numbers expressing quantities of ingredients, properties, and so forth, used to describe and claim certain embodiments of the application are to be understood as being modified in some instances by the term "about," "approximate," or "substantially." Unless otherwise stated, "about," "approximate," or "substantially" may indicate ±20% variation of the value it describes. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

For each of the patents, patent applications, patent application publications and other materials, such as articles, books, instructions, publications, documents, articles, etc., cited in this application are hereby incorporated by reference in their entirety. Application history documents that are inconsistent or conflicting with the contents of the present application are excluded, and documents (currently or later attached to the present application) that limit the widest range of the scope of the present application are also excluded. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the present disclosure are merely illustrative of the principles of the embodiments of the present disclosure. Other modifications that may be employed may be within the scope of the application. Thus, by way of example, but not of limitation, alternative configurations of the embodiments of the application may be utilized in accordance with the teachings herein. Accordingly, embodiments of the present application are not limited to the embodiments that are expressly introduced and described herein.

We claim:

1. A method for determining an energy spectrum of an incident electron beam, implemented on a computing device having at least one processor and at least one storage device, comprising:
   obtaining, from one or more terminals controlled by a user, a plurality of deflection currents of a beam deflection device;
   for each of the plurality of deflection currents,
      determining, by the at least one processor, an energy range of an ejected electron beam, wherein the ejected electron beam is emitted from an output of the beam deflection device after the incident electron beam enters the beam deflection device, and the beam deflection device is configured to filter, through a magnetic field generated by the beam deflection device based on the deflection current, one or more electrons of the incident electron beam to generate the ejected electron beam; and
      obtaining, from a target current test device, a target current of a target generated by the ejected electron beam irradiating the target; and
   determining, by the at least one processor, a plurality of energy sub-ranges of the incident electron beam by dividing the incident electron beam based on the energy ranges of the plurality of ejected electron beams;
   determining, by the at least one processor, a plurality of sub-currents of the incident electron beam based on the plurality of target currents each of which corresponds to one of the plurality of energy ranges of the plurality of ejected electron beams, each sub-current corresponding to an energy sub-range of the plurality of the energy sub-ranges of the incident electron beam; and
   determining, by the at least one processor, the energy spectrum of the incident electron beam based on the plurality of sub-currents corresponding to the plurality of energy sub-ranges of the incident electron beam.

2. The method of claim 1, wherein the determining, by the at least one processor, an energy range of an ejected electron beam for each of the plurality of deflection currents further comprises:
   determining a magnetic field strength of the magnetic field generated by the beam deflection device based on the deflection current;
   determining a center energy value of the energy range of the ejected electron beam based on the magnetic field strength and a deflection radius of the beam deflection device; and
   determining the energy range of the ejected electron beam based on the center energy value and a width of the energy range.

3. The method of claim 1, further comprising:
   obtaining a target deflection current of the beam deflection device;
   determining an energy range of a target ejected electron beam, wherein the target ejected electron beam is emitted from the output of the beam deflection device after the incident electron beam enters the beam deflection device; and
   determining an energy spectrum of the target ejected electron beam based on the energy range of the target ejected electron beam and the energy spectrum of the incident electron beam.

4. The method of claim 1, wherein the determining, by the at least one processor, an energy range of an ejected electron beam for each of the plurality of deflection currents further comprises:
   determining the energy range of the ejected electron beam based the deflection radius of the beam deflection device and the magnetic field.

5. The method of claim 1, wherein the obtaining, from a target current test device, a target current of a target generated by the ejected electron beam irradiating the target includes:
   gradually changing the deflection current of the beam deflection device; and
   successively obtaining the target current flowing through the target after each of the plurality of ejected electron beams irradiates the target.

6. The method of claim 1, wherein the energy ranges of the plurality of ejected electron beams are continuously distributed.

7. The method of claim 1, wherein a start-point of the energy range of the ejected electron beam coincides with an end-point of the energy range of at least one ejected electron beam generated prior to the ejected electron beam, or an end-point of the energy range of the ejected electron beam coincides with a start-point of the energy range of at least one ejected electron beam generated prior to the ejected electron beam.

8. The method of claim 1, wherein
   the target current of the target generated by at least one specific ejected electron beam of the plurality of ejected electron beams irradiating the target is 0, and each of the plurality of ejected electron beams other than the at least one specific ejected electron beam meets at least one of the following conditions:
   (1) the energy range of the each ejected electron beam at least partially overlaps with the energy range of the at least one specific ejected electron beam; or
   (2) a start-point or an end-point of the energy range of the each ejected electron beam coincides with a start-point or an end-point of the energy range of any ejected electron beam generated prior to the each ejected electron beam.

9. A system for determining an energy spectrum of an incident electron beam, comprising a beam deflection device and a computing device, the computing device including a processor, wherein during operations, the processor causes the system to:
   obtain, by the processor, a plurality of deflection currents of the beam deflection device;
   for each of the plurality of deflection currents,
      determine, by the processor, an energy range of an ejected electron beam, wherein the ejected electron beam is emitted from an output of the beam deflection device after the incident electron beam enters the beam deflection device, and the beam deflection device is configured to filter, through a magnetic field generated by the beam deflection device based on the deflection current, one or more electrons of the incident electron beam to generate the ejected electron beam; and obtain, from a target current test device, a target current of a target after the ejected electron beam irradiates the target; and determine, by the processor, a plurality of energy sub-ranges of the incident electron beam by dividing the incident electron beam based on the energy ranges of the plurality of ejected electron beams;

determine, by the processor, a plurality of sub-currents of the incident electron beam based on the plurality of target currents each of which corresponds to one of the plurality of energy ranges of the plurality of ejected electron beams, each sub-current corresponding to an energy sub-range of the plurality of the energy sub-ranges of the incident electron beam; and determine, by the processor, the energy spectrum of the incident electron beam based on the plurality of sub-currents corresponding to the plurality of energy sub-ranges of the incident electron beam.

10. The system of claim 9, wherein to determine an energy range of an ejected electron beam, the processor causes the system further to:

determine a magnetic field strength of the magnetic field generated by the beam deflection device based on the deflection current;

determine a center energy value of the energy range of the ejected electron beam based on the magnetic field strength and a deflection radius of the beam deflection device; and determine the energy range of the ejected electron beam based on the center energy value and a width of the energy range.

11. The system of claim 9, the processor causes the system further to:

obtain a target deflection current of the beam deflection device;

determine an energy range of a target ejected electron beam, wherein the target ejected electron beam is emitted from the output of the beam deflection device after the incident electron beam enters the beam deflection device; and determine an energy spectrum of the target ejected electron beam based on the energy range of the target ejected electron beam and the energy spectrum of the incident electron beam.

12. The system of claim 9, wherein to determine an energy range of an ejected electron beam, the processor causes the system further to:

determine the energy range of the ejected electron beam based on the deflection radius of the beam deflection device and the magnetic field.

13. The system of claim 9, wherein to obtain a target current of a target after the ejected electron beam irradiates the target, the processor causes the system further to:

gradually change the deflection current of the beam deflection device; and successively obtain the target current flowing through the target after each of the plurality of ejected electron beams irradiates the target.

14. The system of claim 9, wherein the energy ranges of the plurality of ejected electron beams are continuously distributed.

15. The system of claim 9, wherein a start-point of the energy range of the ejected electron beam coincides with an end-point of the energy range of at least one ejected electron beam generated prior to the ejected electron beam, or an end-point of the energy range of the ejected electron beam coincides with a start-point of the energy range of at least one ejected electron beam generated prior to the ejected electron beam.

16. The system of claim 9, wherein
the target current of the target generated by at least one specific ejected electron beam of the plurality of ejected electron beams irradiating the target is 0, and each of the plurality of ejected electron beams other than the at least one specific ejected electron beam meets at least one of the following conditions:

(1) the energy range of the each ejected electron beam at least partially overlaps with the energy range of the at least one specific ejected electron beam; or (2) a start-point or an end-point of the energy range of the each ejected electron beam coincides with a start-point or an end-point of the energy range of any ejected electron beam generated prior to the each ejected electron beam.

17. A non-transitory computer readable medium comprising executable instructions that, when executed by at least one processor, cause the at least one processor to effectuate a method comprising:

obtaining, from one or more terminals controlled by a user, a plurality of deflection currents of a beam deflection device;

for each of the plurality of deflection currents,
determining, by the at least one processor, an energy range of an ejected electron beam, wherein the ejected electron beam is emitted from an output of the beam deflection device after an incident electron beam enters the beam deflection device, and the beam deflection device is configured to filter, through a magnetic field generated by the beam deflection device based on the deflection current, one or more electrons of the incident electron beam to generate the ejected electron beam; and obtaining, from a target current test device, a target current of a target generated by the ejected electron beam irradiating the target; and determining, by the at least one processor, a plurality of energy sub-ranges of the incident electron beam by dividing the incident electron beam based on the energy ranges of the plurality of ejected electron beams;

determining, by the at least one processor, a plurality of sub-currents of the incident electron beam based on the plurality of target currents each of which corresponds to one of the plurality of energy ranges of the plurality of ejected electron beams, each sub-current corresponding to an energy sub-range of the plurality of the energy sub-ranges of the incident electron beam; and determining, by the at least one processor, the energy spectrum of the incident electron beam based on the plurality of sub-currents corresponding to the plurality of energy sub-ranges of the incident electron beam.

18. The non-transitory computer readable medium of claim 17, wherein the energy ranges of the plurality of ejected electron beams are continuously distributed.

19. The method of claim 1, wherein the beam deflection device includes an energy slit corresponding to the magnetic field, wherein a position of the energy slit corresponds to a deflection radius of the beam deflection device, and the energy slit is configured to permit electrons in the incident electron beam whose deflection radius under the magnetic field fall within a range, the range corresponding to the deflection radius of the beam deflection device, to pass through.

20. The system of claim 9, wherein the beam deflection device includes an energy slit corresponding to the magnetic field, wherein a position of the energy slit corresponds to a deflection radius of the beam deflection device, and the energy slit is configured to permit electrons in the incident electron beam whose deflection radius under the magnetic field fall within a range, the range corresponding to the deflection radius of the beam deflection device, to pass through.

\* \* \* \* \*